United States Patent [19]

Arentzen et al.

[11] Patent Number: 5,243,037
[45] Date of Patent: Sep. 7, 1993

[54] POLY(FLUOROALKYL) SUGAR REAGENTS FOR SURFACE MODIFICATION OF SUPPORTS

[75] Inventors: Rene Arentzen; Prabhakar K. Jadhav; Robert K. Kobos; Bruce E. Smart, all of Wilmington, Del.

[73] Assignee: E. I. Du Pont de Nemours and Company, Wilmington, Del.

[21] Appl. No.: 586,173

[22] Filed: Sep. 21, 1990

[51] Int. Cl.$^5$ .................. C07H 15/00; C12N 11/08; C12N 11/06
[52] U.S. Cl. .................................. 536/18.4; 435/180; 435/181
[58] Field of Search ............... 435/174, 177, 180, 181; 536/18.4

[56] References Cited

U.S. PATENT DOCUMENTS

| | | |
|---|---|---|
| 3,843,443 | 10/1974 | Fishman ............................ 195/63 |
| 4,317,879 | 3/1982 | Busby et al. ...................... 435/14 |
| 4,619,897 | 10/1986 | Hato et al. ....................... 435/182 |
| 4,619,904 | 10/1986 | Giaever et al. ................... 436/518 |
| 4,885,250 | 12/1989 | Eveleigh et al. .................. 435/181 |

FOREIGN PATENT DOCUMENTS

| | | |
|---|---|---|
| 0263184 | 4/1988 | European Pat. Off. . |
| 0363052 | 4/1990 | European Pat. Off. . |
| 8603840 | 7/1986 | World Int. Prop. O. . |

OTHER PUBLICATIONS

Kennedy, et al., Solid Phase Biochemistry, Analytical and Synthetic Aspects, Scouten, Ed., (1983), pp. 253-391.
Danielson, et al., Biotechnol. Bioeng. 23:1913-1917 (1981).
Siergeiej, Diss. Abs. Int. B., vol. 44, p. 153 (1983).
De Miguel, et al., Chromatographia, vol. 24, pp. 849-853 (1987).

*Primary Examiner*—David M. Naff
*Attorney, Agent, or Firm*—Barbara C. Siegell

[57] ABSTRACT

Poly(fluoroalkyl) sugar reagents are prepared containing a sugar such as a monosaccharide or a disaccharide to which are bonded multiple fluoroalkyl anchor groups capable of attaching to a fluorocarbon surface, and either a reactive group capable of covalent coupling to a biomolecule or a charged group to form an ion-exchanger or a non-ionic group to give a neutral fluorosurfactant. A spacer may be between the reactive group and the sugar. The poly(fluoroalkyl) sugar reagents are strongly adsorbed onto fluorocarbon surfaces to provide supports for such applications as separation and immobilization of biomolecules such as enzymes, carrying out heterogeneous diagnostic assays, and preparation of biosensors.

4 Claims, No Drawings

POLY(FLUOROALKYL) SUGAR REAGENTS FOR SURFACE MODIFICATION OF SUPPORTS

TECHNICAL FIELD

This invention relates to a novel group of poly(fluoroalkyl) sugar reagents, a method for their use for the modification of the surface of solid or liquid supports, and supports used for application in the separation of biomolecules, enzyme immobilization, heterogeneous diagnostic assays, and biosensors.

BACKGROUND ART

Numerous methods have been developed for the immobilization of proteins and other biomolecules onto solid or liquid supports. A description of these methods can be found in general reviews such as that given by Mosbach, 1976, Methods in Enzymology, Vol. 44; Weetall, 1975, Immobilized Enzymes, Antigens, Antibodies, and Peptides; or Kennedy et al., 1983, Solid Phase Biochemistry, Analytical and Synthetic Aspects, Scouten, ed., pp. 253-391. The most commonly used methods are adsorption or covalent binding to the support.

Adsorption is the oldest and simplest method for protein immobilization. To effect immobilization, a solution of the protein is contacted with a support material such as alumina, carbon, an ion-exchange resin, cellulose, glass or a ceramic. Although the immobilization procedure may be simple, the interactions involved in the adsorption process are complex and include charge-charge, van der Waals and hydrophobic interactions, and hydrogen bonding. The adsorption method has the advantages of low cost, extreme simplicity, mild immobilization conditions and the ability to regenerate the support. The main limitation of this method is the relatively weak interaction between the protein and the support, which may result in desorption of the protein upon changes in pH and ionic strength. The often undefined nature of these interactions also can limit their use.

The most frequently used immobilization technique is the covalent binding of the protein to chemically activated solid supports such as glass, synthetic polymers, and cross-linked polysaccharides. (Generally, this technique results in a protein which is immobilized in a more stable fashion than protein immobilized by adsorption.) An example of this method is the cyanogen bromide activation of polysaccharide supports, e.g., agarose.

Although these traditional supports have been used in many applications, they suffer from some limitations. The polysaccharide supports are compressible, which limits their application in column configurations at high flow rates. These supports are also susceptible to microbial attack. Silica supports are not stable under alkaline conditions. Polymeric supports are also not chemically inert, and usually have a specific gravity close to 1, which results in long settling times in batch operations. Moreover, all of these supports exhibit varying degrees of nonspecific binding of unwanted proteins. The use of solid and liquid fluorocarbon supports overcome many of these limitations. Fluorocarbons are chemically inert and mechanically stable. The high specific gravity of fluorocarbon supports results in rapid settling in batch operations. However, it is difficult to activate fluorocarbon supports for immobilization.

Fluorocarbon polymers have been used as supports to which biomolecules have been attached by adsorption [Fishman U.S. Pat. No. 3,843,443, issued on Oct. 22, 1974; WO 8603-840-A filed by Rijskuniv Groningen; Danielson and Siergiej, Biotechnol. Bioeng. 23, 1913-1917 (1981); Siergeiej, Dissertation Abstracts, Int. B., Volume 44, 153 (1983)]. Because these methods rely on simple adsorption of the biomolecule onto the support, the attachment is relatively weak. Consequently, some or all of the immobilized biomolecule is lost during use. In addition, a significant loss of biological activity of the biomolecule results upon adsorption.

Busby et al. (U.S. Pat. No. 4,317,879, issued Mar. 2, 1982) disclose the covalent attachment of the enzyme glucose oxidase to a fluorocarbon membrane. The membrane was first etched with a sodium dispersion in naphthalene, followed by paraformaldehyde linking of the enzyme. This method requires severe chemical conditions to activate the fluorocarbon surface for covalent binding to the enzyme.

Hato et al., (U.S. Pat. No. 4,619,897, issued Oct. 23, 1986) disclose the immobilization of enzymes onto a fluorine resin membrane which is made hydrophilic on one side by penetration of a perfluoroalkyl surface active agent to a prescribed depth. The asymmetrically functional membrane obtained is then treated with an enzyme and a cross-linking agent such as glutaraldehyde to effect immobilization. In this approach, the fluorocarbon surface is not activated for covalent attachment of the enzyme. Rather, the enzyme is cross-linked within the pores of the wetted membrane. This approach is limited to porous fluorocarbon membranes.

The use of perfluorocarbon polymer-based supports for enzyme immobilization and affinity chromatography is described in U.S. Pat. No. 4,885,250 issued Dec. 5, 1989. In this method the biomolecule is first modified by reaction with a perfluoroalkylating agent such as perfluorooctylpropylisocyanate described in copending application Ser. No. 134,028, now U.S. Pat. No. 4,954,444. Then, the modified protein is adsorbed onto the fluorocarbon support to effect immobilization. This procedure works well for the immobilization of many biomolecules, particularly immunoglobulins. However, substantial loss of biological activity results for some proteins because of the need to use organic solvents (16% v/v) in the perfluoroalkylation reaction, the hydrophobic nature of the fluorocarbon support, and the need for multipoint modification of protein to obtain secure immobilization. Multipoint modification of the biomolecule is required because of the mono(fluoroalkyl) reagents used. In addition, the mono(fluoroalkyl) reagents desorb from the support in the presence of high levels of organic solvents, e.g., about 50% or greater.

A revised method for immobilization onto fluorocarbon surfaces or non-fluorocarbons which contain a fluorocarbon interlayer attached to the surface of the core has been described in copending application Ser. No. 413,867, now U.S. Pat. No. 5,079,155. In this revised method, a perfluoroalkylating reagent containing a mono(fluoroalkyl) anchor group, a hydrophilic spacer arm, and a reactive group for covalent coupling to the protein is adsorbed onto the surface of the support. An aqueous solution of the protein is added to effect immobilization. This approach overcomes many of the limitations of the original method. Higher retention of activity, particularly for enzymes, is obtained because totally aqueous solutions of the enzyme are used, and the surface of the support is more hydrophilic. This approach also provides a preactivated support which is more convenient to use. However, the support with the adsorbed reagent is not stable because the reagent is secured by only one fluoroalkyl anchor group. In addition, multipoint attachment of the biomolecule is required for secure immobilization.

In copending application Ser. No. 413,867 a method for forming solid supports for size exclusion and ion-exchange separations is described. The support is prepared by forming a fluorocarbon interlayer by attaching a fluorocarbon to the surface of a solid carrier, followed by treatment with a fluorosurfactant. The use of a neutral fluorosurfactant results in a size exclusion support, while a charged fluorosurfactant provides an ion-exchange support. The stability of these supports is limited because of the mono(fluoroalkyl) anchor group which adsorbs to the fluorocarbon surface.

Giaver, (U.S. Pat. No. 4,619,904, issued Oct. 28, 1986) describes the use of fluorocarbon emulsions in agglutination immunoassays. The emulsions were formed by adding a fluorinated polar molecule such as pentafluorobenzoyl chloride to a fluorocarbon liquid. The resulting emulsion was contacted with an aqueous solution of the protein. Again, mono(fluoroalkyl) anchor groups were used to immobilize the protein.

Lowe et al. in copending application Ser. No. 428,154, describe the attachment of biomolecules to fluorocarbon surfaces by means of a polymer such as poly(vinyl alcohol), which has been chemically modified to contain a significant number of perfluoroalkyl groups. Although this approach provides multiple fluoroalkyl anchor groups for secure attachment to the fluorocarbon surface, the number of anchor groups is difficult to control and reproduce.

De Miguel et al., Chromatographia, Vol. 24, 849–853, 1987, describe the strong retention of phenyl-D-glucopyranoside, modified with multiple fluorocarbon chains, on fluorocarbon bonded phases under reversed phase conditions. The authors speculate that such strong retention may allow dynamic anchoring of biomolecules. No examples were provided. The compounds described cannot be used for immobilization because they contain no reactive group to couple to the biomolecule. The major difference between the phenyl-D-glucopyranosides of De Miguel et al., and the present invention is that their compounds do not contain a spacer arm and reactive group for covalent binding to the biomolecule.

One object of this invention is to provide a superior composition for modifying fluorocarbon surfaces that permit good retention of biomolecules.

Another object of this invention is to provide a reagent for facilitating immobilization of biomolecules on a support with retention of biological activity.

Yet another object of this invention is to provide a method for forming a solid support using the superior reagents described herein.

Still another object of this invention is to provide a process for immobilizing a biomolecule onto a fluorocarbon surface.

SUMMARY OF THE INVENTION

This invention relates to poly(fluoroalkyl) sugar reagents for modification of the surfaces of supports used in immobilizing biomolecules.

The poly(fluoroalkyl) sugar reagents claimed in this invention are comprised of a sugar template to which are bonded multiple fluoroalkyl anchor groups and an optional spacer, attached to a reactive group to covalently bind to biomolecules, a charged group to form an ion-exchanger, or a non-ionic group to give a neutral fluorosurfactant.

These reagents are adsorbed onto fluorocarbon surfaces to provide supports for such applications as the separation of biomolecules, enzyme immobilization, heterogeneous diagnostic assays, and biosensors.

The reagents and supports described herein offer advantages over those of the prior art because the poly(fluoroalkyl) sugar reagents are adsorbed on fluorocarbon support surfaces more strongly than mono(fluoroalkyl) reagents. Examples of novel compositions claimed herein are as follows:

(a) a composition of the structure:

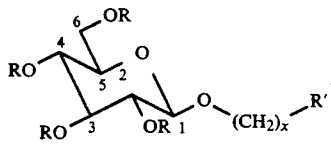

wherein:
R is selected from

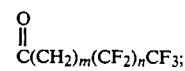

$m = 1-5$;
$n = 3-20$;
$x = 1-10$; and
R' is selected from the following structures:

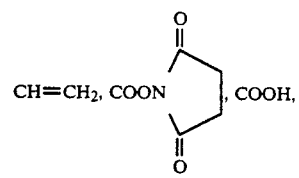

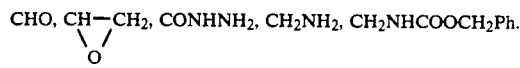

(b) a composition of the structure:

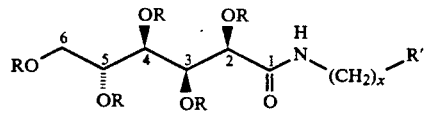

wherein:
R is selected from $CO(CH_2)_m(CF_2)_nCF_3$;
$x = 1-10$;
$m = 1-5$;
$n = 3-20$; and
R' is

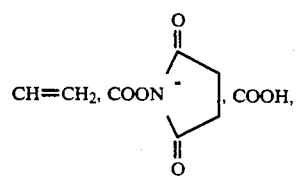

-continued

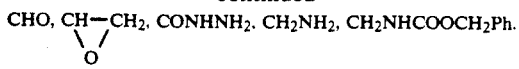

(c) a composition of the structure:

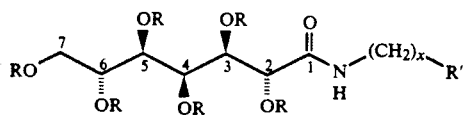

wherein:
R is $CO(CH_2)_m(CF_2)_nCF_3$;
x=2-10; and
R' is selected from

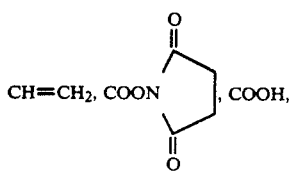

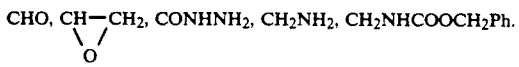

(d) a composition of the structure:

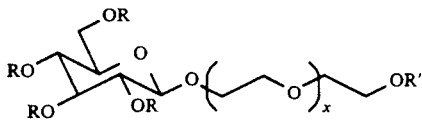

wherein:
R is $CO(CH_2)_m(CF_2)_nCF_3$;
m=1-5;
n=3-20;
R' is $CH_2OCH_2Ph$, H, phenyl, $CH_3$ or $C_2H_5$; and
x=1-20.

The invention also concerns:
(1) a support containing an attached binder for a biomolecule consisting essentially of:
(a) a fluorocarbon surface; and
(b) a polyfluoro sugar composition comprised of a sugar template to which are attached multiple fluoroalkyl anchor groups securely attached to the surface of said fluorocarbon interlayer, said sugar template further consisting of a spacer containing a reactive group capable of coupling to a biomolecule.

(2) a process for immobilizing a biomolecule on a fluorocarbon surface comprising the steps of:
(a) activating the fluorocarbon surface by contacting the fluorocarbon surface with a reactive poly(fluoroalkyl) sugar reagent containing a sugar template to which are attached a plurality of fluoroalkyl anchor groups, an optional spacer and a reactive group by causing the fluorocarbon surface to adsorb the reagent; then
(b) adding a solution of a biomolecule to the activated fluorocarbon surface to attach to the sugar reagent to immobilize the biomolecule on the fluorocarbon surface.

(3) a process for immobilizing a biomolecule on a fluorocarbon surface comprising the step of:

(a) attaching a poly(fluoroalkyl) sugar reagent to a biomolecule to form a conjugate; and then
(b) adsorbing the resulting conjugate on a fluorocarbon surface.

DESCRIPTION OF INVENTION

The poly(fluoroalkyl) sugar reagents claimed in this invention contain a sugar template to which are attached multiple fluoroalkyl anchor groups. The sugar can be a monosaccharide, such as glucose, mannose, galactose, gluconic acid, and glucoheptanoic acid, a disaccharide, such as maltose and lactose, or any polyhydroxy compound with a well-defined number of hydroxyl groups. These structures permit the attachment of multiple fluoroalkyl anchor groups. For example, glucose, gluconic acid and glucoheptanoic acid allow attachment of four, five and six perfluoroalkyl anchor groups, respectively. The glucoheptanoic acid reagent is preferred because the six fluoroalkyl groups provide the most secure attachment of the reagent to the fluorocarbon surface.

The sugar reagents may be dissolved in an aqueous or mixed organic solvent (see Example 1).

The sugar reagent group is a moiety containing at one end, a highly fluorinated anchor group, such as perfluorobutyl, perfluorohexyl, or perfluorooctyl, capable of attaching to a fluorocarbon surface and at the other end, a reactive group capable of covalent coupling to the biomolecule. Examples of reactive groups include: carboxylic acid, amine, acylhydrazide, aldehyde, an active ester such as N-acyloxysuccinimide, acylimidazolide and epoxide. The anchor portion and the reactive group can be separated by a spacer group. Alternatively, reagents with a polyoxyethylene group can be used as neutral surfactants to prepare supports for size exclusion chromatography. Charged groups, such as quaternary ammonium ion and carboxylic acids, are used to prepare ion-exchange supports useful in ion-exchange chromatography and ion-exchange membranes.

A general method of forming the solid or liquid support of this invention useful for bioseparations, enzyme immobilization, diagnostic assays, and biosensors, is to first activate the fluorocarbon support by adsorbing the poly(fluoroalkyl) sugar reagent onto the surface. The poly(fluoroalkyl) reagents are adsorbed much more strongly than mono(fluoroalkyl) anchor reagents. The poly(fluoroalkyl) reagents adsorb onto fluorocarbon surfaces in the presence of high concentrations of organic solvents, e.g., acetone, 50 to 90%, while mono(fluoroalkyl) reagents are desorbed from the fluorocarbon surface in the presence of high levels of organic solvent, e.g., acetone, 50% or greater. To effect immobilization, an aqueous solution of the biomolecule is added to the activated fluorocarbon support.

A poly(fluoroalkyl) sugar reagent with a poly(oxyethylene) group, e.g., reagent 38, a neutral fluorosurfactant, can be coimmobilized along with the reactive poly(fluoroalkyl) sugar, to minimize nonspecific binding of other proteins and to improve the retention of biological activity of the immobilizing reagent.

The surfactant also renders the surface more hydrophilic which improves the wettability of the support. Alternatively, a mono(fluoroalkyl) neutral fluorosurfactant, such as Zonyl ® FSN fluorosurfactant, a fluoroalkyl-polyoxyethylene surfactant, can be added to the poly(fluoroalkyl) sugar reagent solution, the solution of the biomolecule to be immobilized, or the support can be treated with the fluorosurfactant in a separate step either after or just preceding the immobilization step.

The fluorocarbon surface can be a solid fluorocarbon polymer such as poly(tetrafluoroethylene), a liquid fluorocarbon such as perfluorodecalin, or a nonfluorocarbon support that is coated with a fluorocarbon interlayer.

The non-fluorocarbon core for preparing solid supports of this invention include inorganic surfaces such as silica, magnetic particles and polymers such as polystyrene, polypropylene and polyethylene. By interlayer is meant a layer of fluorocarbon coating located on the surface of the non-fluorocarbon solid carrier core. The fluorocarbon compound can be a fluoropolymer, fluorosilane or other highly fluorinated hydrocarbon chain. The interlayer may be applied to a non-fluorocarbon solid by spray coating or by chemical reactions. A sufficient amount of fluorocarbon surface must be present to secure the reagent and anchor the biomolecule.

The poly(fluoroalkyl) sugar reagents of the present invention can be used in the preparation of supports for the separation of biomolecules, enzyme immobilization, heterogeneous diagnostic assays and biosensors.

The main advantages of the poly(fluoroalkyl) sugar reagents over the mono(fluoroalkyl) reagents are: higher retention of biological activity, higher immobilization efficiency, more secure attachment of the biomolecule, a more stable preactivated support, and a simpler immobilization procedure. The supports described in this invention can be used for various kinds of extracorporeal depletion therapy, for nucleic acid hybridization assays, to capture DNA or RNA from mixtures and for various configurations of solid and liquid phase bioassays.

Below are the Experimental details for the synthesis of poly(fluoroalkyl) sugar reagents. The reagents will be numbered as shown below throughout the specification.

REAGENTS

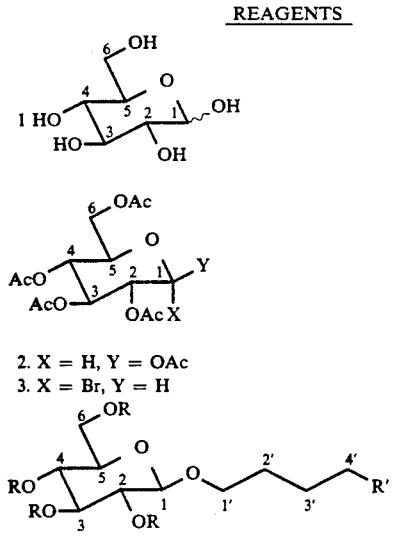

2. X = H, Y = OAc
3. X = Br, Y = H

4. R = Ac, R' = CH=CH$_2$
5. R = H, R' = CH=CH$_2$
6. R = COCH$_2$CH$_2$(CF$_2$)$_7$CF$_3$; R' = CH=CH$_2$
7. R = COCH$_2$CH$_2$(CF$_2$)$_7$CF$_3$; R' = COOH

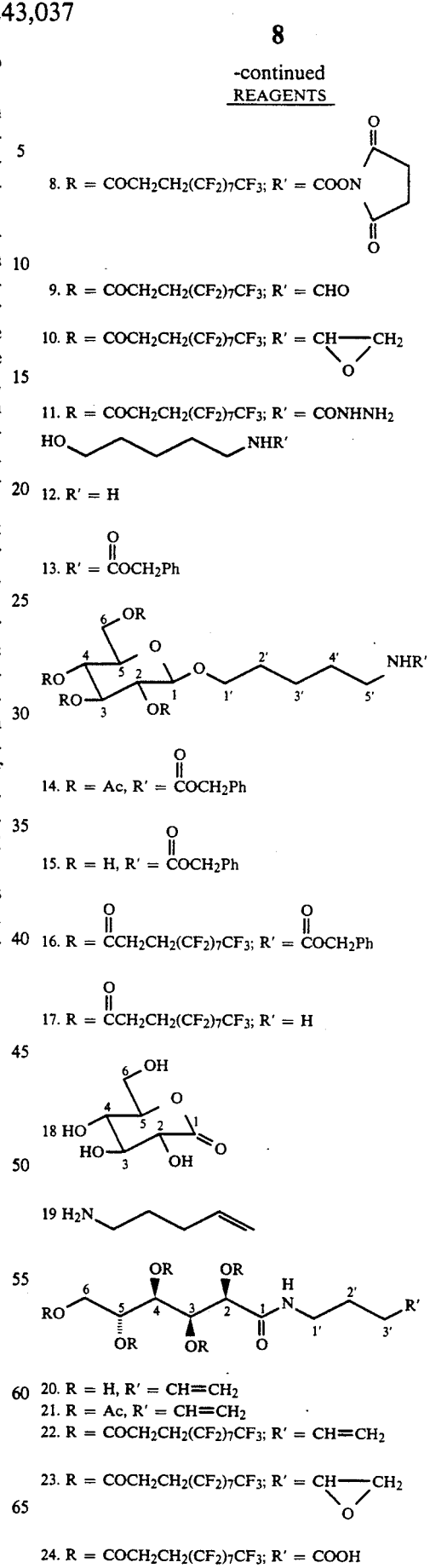

8. R = COCH$_2$CH$_2$(CF$_2$)$_7$CF$_3$; R' = COON(succinimide)

9. R = COCH$_2$CH$_2$(CF$_2$)$_7$CF$_3$; R' = CHO

10. R = COCH$_2$CH$_2$(CF$_2$)$_7$CF$_3$; R' = CH—CH$_2$ (epoxide)

11. R = COCH$_2$CH$_2$(CF$_2$)$_7$CF$_3$; R' = CONHNH$_2$

12. R' = H

13. R' = COCH$_2$Ph

14. R = Ac, R' = COCH$_2$Ph

15. R = H, R' = COCH$_2$Ph

16. R = CCH$_2$CH$_2$(CF$_2$)$_7$CF$_3$; R' = COCH$_2$Ph

17. R = CCH$_2$CH$_2$(CF$_2$)$_7$CF$_3$; R' = H 18. (sugar structure)

19. H$_2$N~~~~

20. R = H, R' = CH=CH$_2$
21. R = Ac, R' = CH=CH$_2$
22. R = COCH$_2$CH$_2$(CF$_2$)$_7$CF$_3$; R' = CH=CH$_2$
23. R = COCH$_2$CH$_2$(CF$_2$)$_7$CF$_3$; R' = CH—CH$_2$ (epoxide)
24. R = COCH$_2$CH$_2$(CF$_2$)$_7$CF$_3$; R' = COOH -continued
REAGENTS 25. R = COCH$_2$CH$_2$(CF$_2$)$_7$CF$_3$; R' = COON 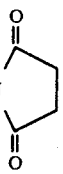

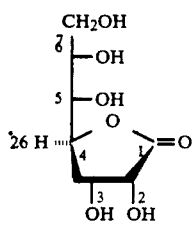
26

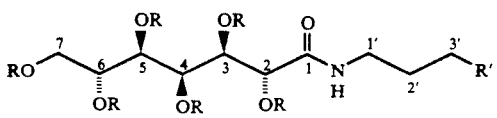

27. R = H, R' = CH=CH$_2$
28. R = Ac, R' = CH=CH$_2$
29. R = COCH$_2$CH$_2$(CF$_2$)$_7$CF$_3$; R' = CH=CH$_2$

30. R = COCH$_2$CH$_2$(CF$_2$)$_7$CF$_3$; R' = CH—CH$_2$
                                              \ /
                                               O

31. R = COCH$_2$CH$_2$(CF$_2$)$_7$CF$_3$; R' = COOH

32. R = COCH$_2$CH$_2$(CF$_2$)$_7$CF$_3$; R' = COON 

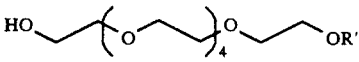

33. R' = H
34. R' = CH$_2$OCH$_2$Ph

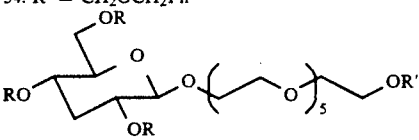

35. R = Ac; R' = CH$_2$OCH$_2$Ph
36. R = H; R' = CH$_2$OCH$_2$Ph
37. R = COCH$_2$CH$_2$(CF$_2$)$_7$CF$_3$; R' = CH$_2$OCH$_2$Ph
38. R = COCH$_2$CH$_2$(CF$_2$)$_7$CF$_3$; R' = H

D-glucose 1, 1,2,3,4,6-penta-O-acetyl-β-D-glucopyranoside 2, gluconolactone 18 and glucoheptanolactone 26 are commercially available and were purchased from Aldrich Chemical Company.

2,3,4,6-Tetra-O-Acetyl-β-D-Glucopyranosyl Bromide 3

In a 250-mL round-bottom flask equipped with a magnetic stirring bar were placed 2 (19.577 g, 50 mmol), acetic anhydride (12.5 mL) and hydrogen bromide (75 mL, 30–32% solution by weight in glacial acetic acid) and allowed to stir at room temperature for 24 h. It was then poured into ice-cold dichloromethane (~100 mL) in a separatory funnel, washed with ice-cold water (3×75 mL), saturated sodium bicarbonate. The residue after drying and removal of solvent was crystallized from a mixture of diethyl ether and hexane to provide 3 (16.96 g, 82.7% yield). The compound 3 was identified by $^1$H NMR.

5'-Hexenyl 2,3,4,6-Tetra-O-Acetyl-β-D-Glucopyranoside 4

In a 500-mL round-bottom flask equipped with overhead mechanical stirrer and addition funnel were placed silver carbonate (11.03 g, 40 mmol), anhydrous calcium sulfate (drierite, ground with a mortar and pestle then vacuum dried for an hour), 5-hexen-1-ol (4.8 mL, 40 mmol) and anhydrous dichloromethane (100 mL). Meanwhile, compound 3 (8.2 g, 20 mmol) was dissolved in 75 mL of dichloromethane and added dropwise to the above mixture over a 2-h period, and the solution stirred vigorously for 48 h. The reaction mixture was filtered and the residue after removal of the solvent chromatographed (silica gel 300 g, 1:3 ethyl acetate/hexane) to provide 4 (4.95 g, 57.5% yield).

$^1$H NMR (300 MHz; CDCl$_3$ δ1.43 (m, 2H, H-3), 1.583 (m, 2H, H-2'), 2.007, 2.025, 2.037, 2.087 (4 s+m, 14H, 4 OAc,+H-4'), 3.479 (1H, m, H-1'A), 3.689 (m, 1H, H-5), 3 886 (m, 1H, H-1'B), 4.135 (dd, 1H, H-6A, $J_{H-6A,H-6B}$=12.2 Hz; $J_{H-6A,H-5}$=1.7 Hz), 4.266 (dd, 1H, H-6B, $J_{H-6B,H-6A}$=12.3 Hz, $J_{H-6B,H-5}$=4.7 Hz), 4.493 (d, 1H, H-1', $J_{H-1',H-2'}$=7.9 Hz), 4.968 (m, 3H, 2×H-6'+H-2), 5.086 (dd, 1H, H-4, J=H-4, H-5=$J_{H-4,H-3}$=9.6 Hz), 5.207 (dd, 1H, H-3, $J_{H3-4}$=$J_{H-3,H-2}$=9.4 Hz), 5.782 (m, 1H, H-5').

IR (nujol) 1755 (C=O), 1640 (C=C), 1220, 1040 (C—O—C) cm$^{-1}$.

$^{13}$C NMR (75 MHz, CDCl$_3$) δ20.559 (OCOCH$_3$) 25.128 (C-3'), 28.845 (C-2'), 33.268 (C-4'), 62.127 (C-6), 68.699, 69.834, 69.852, 71.496, 71.868, 72.987 (C-1', C-2, C-3, C-4, C-5), 100.826 (C-1), 114.582 (C-6'), 138.437 (C-5'), 169.100, 169.259, 170.132, 170.160 (OCOCH$_3$).

5'-Hexenyl β-D-Glucopyranoside 5

In a 250-mL round-bottom flask equipped with a magnetic stirring bar, nitrogen inlet and bent-tube adapter were placed 4 (4.29 g, 9.97 mmol), methanol (anhydrous 100 mL) and sodium methoxide (0.5N in methanol, 1.0 mL) and stirred at room temperature for 1.25 h. Then it was treated with 2.0 g of Bio-Rad ion exchange resin AG-50W-X8 and stirred for 10 min. The reaction mixture was filtered, washed with methanol, and the solvent removed. The residue was dried under vacuum 0.1 mm Hg/18 h to provide 5 (2.56 g, 98% yield).

$^1$H NMR (300 MHz, D$_2$O) δ1.483 (m, 2H, H-3'), 1.666 (m, 2H, H-2'), 2.115 (dd, 2H, H-4', $J_{H-4',H-5'}$=13.7 Hz, $J_{H-4',H-3'}$=6.9 Hz), 3.270 (t, 1 H), 3.469 (m, 3 H), 3.718 (m, 2 H), 3.930 (m, 2 H), (H-1'A, H-1'B, H-2, H-3, H-4, H-5, H-6A, H-6B), 4.464 (d, 1H, H-1, $J_{H1,H2}$=8.0 Hz), 5.038 (m, 2H, H-6'), 5.943 (m, 1H, H-5').

$^{13}$C NMR (75 MHz, D$_2$O) δ26.713 (C-3'), 30.547 (C-2'), 34.93 (C-4'), 63.162 (C-6), 63.162, 72.035, 72.642, 75.468, 78.177 (C-1', C-2, C-3, C-4, C-5), 104.469 (C-1), 116.656 (C-6'), 142.055 (C-5').

IR (nujol) 3470, 3350 (OH), 1640 (C=C), 1080, 1035 (C—O—C).

FAB MS calcd for C12H2206 (M+H) 263.15. Found 263.28.

5'-Hexenyl 2,3,4,6-Tetra-O(3-Perfluorooctyl)Propionyl-β-D-Glucopyranoside 6

In a 250-mL round-bottom flask equipped with a magnetic stirring bar and bent-tube adapter were placed 5 (2.4 g, 9.15 mmol), dimethylaminopyridine (5.58 g, 45 mmol), perfluorooctylpropionic acid (22.49 g, 45.7 mmol), molecular sieves 4 Å powder (500 mg), anhydrous dimethylformamide (25 mL) and Freon®-113 (1,1,2-trichlorotrifluoroethane, 25 mL). The mixture was cooled to ~0° C and dicyclohexylcarbodiimide (11.33 g, 54.9 mmol) suspended in DMF and Freon®-113 (25 mL+25 mL) was added to the above mixture. The contents were stirred at room temperature for 25 h. The mixture was filtered and the residue chromatographed on silica gel (325 g, 1:12 ethyl acetate/Freon®-113) to provide 6 (14.34 g, 72.6% yield).

$^1$H NMR (300 MHz, CDCl$_3$+Freon®-113) 1.2–2.0 (bm, 4H, H-2', H-3'), 2.061 (m, 2H, H-4'), 2.599 (m, 16H, 4 X-COCH$_2$CH$_2$(CF$_2$)—), 3.494 (m, 1H, H-1'A), 3.725 (br m, 1H, H-5), 3.919 (m, 1H, H-1'B), 4.179 (dd, 1H, H-6A, $J_{H-6A,H-6B}$=12.4 Hz, $J_{H-6A,H-5}$=1.7 Hz), 4.480 (dd, 1H, H-6B, $J_{H-6B,H-6A}$=12.5 Hz, $J_{H-6B,H-5}$=4.0 Hz), 4.537 (d, 1H, H-1, $J_{H-1,H-2}$=7.9 Hz), 4.96 (m, 2H, H-6'), 5.074 (dd, 1H, H-2, $J_{H-2,H-1}$=8.7 Hz), 5.185 (dd, 1H, H-4, $J_{H-4,H-3}$=$J_{H-4,H-5}$=9.6 Hz), 5.289 (dd, 1H, H-3, $J_{H-3,H-4}$=$J_{H-3,H-2}$=9.3 Hz), 5.779 (m, 1H, H-5').

$^{13}$C NMR (75 MHz, CDCl$_3$+Freon®-113) δ24.485 (C-3'), 29.068 (C-2'), 33.057 (C-4'), 62.244 (C-6), 69.010, 70.278, 72.187, 72.409, 73.919 (C-1', C-2, C-3, C-4, C-5), 100.59 (C-1), 114.414 (C-6'), 137.836 (C-5'), 169.857, 170.306, 170.953, 171.102 (4×OCOCH$_2$CH$_2$).

IR (KBr) 1755 (OCOR), 1200 (—CF$_2$—), 1150 cm$^{-1}$.

FAB MS calcd for C$_{56}$H$_{34}$F$_{68}$O$_{10}$ (M+H) 2059.8. Found 2059.6.

4'-(Carboxy)Butyl 2,3,4,6-Tetra-O-(3-Perfluorooctyl)Propionyl-β-D-Glucopyranoside 7

In a 1-liter, 3-necked, round-bottom flask equipped with an overhead mechanical stirrer, reflux condenser and nitrogen inlet were placed 6 (13.34 g, 6.18 mmol), Aliquat® 336 (1.50 g, Aliquat® 336 is a phase transfer catalyst available from Aldrich Chemical Co.), glacial acetic acid (45 mL), 1,1,2-trichlorotrifluoroethane (150 mL), hexane (150 mL) and cooled to -5° C in an icebath. Meanwhile potassium permanganate (23.706 g, 150 mmol) was dissolved in 300 mL of water and then added slowly to the above mixture with vigorous stirring. After the addition has been completed, the contents were stirred in the same bath at room temperature for 24 h. The excess potassium permanganate was decomposed by the addition of sodium sulfite (30 g) in small portions (cooling may be required). After stirring the contents for 15 min, the reaction mixture was acidified with 1:1 hydrochloric acid/water while cooling the mixture in waterbath (~20° C.). The reaction mixture was diluted with ethyl ether (200 mL) and then poured into a separatory funnel (use brine to break up emulsions if necessary). The organic layer was washed with water, brine and dried over magnesium sulfate. The residue was dried under vacuum (1 mm) for 3 days (to make it free from acetic acid) to provide 7 (12.37 g, 92% yield) as white solid which was used in the following step without further purification.

$^1$H NMR (300 MHz, Acetone-D$_6$+Freon®-113) δ1.0–1.8 (m, 4H, H-2'+H-3'), 2.284 (m, 2H, H-4'), 2.599 (m, 16H, 4×OCOCH$_2$CH$_2$CF$_2$—), 3.583 (m, 1H, H-1'A), 3.897 (m, 1H, H-1'B), 4.045 (m, 1H, H-5), 4.225 (dd, 1H, H-6A, $J_{H-6A,H-6B}$=12.4 Hz, $J_{H-6A,H-5}$=1.8 Hz), 4.470 (dd, 1H, H-6B, $J_{H-6B,H-6A}$=12.4 Hz, $J_{H-6B,H-5}$=4.2 Hz), 4.817 (d, 1H, H-1, J=8 Hz) 5.029 (dd, 1H, H-2, $J_{H-2,H-3}$=9.5 Hz, $J_{H-2,H-1}$=8.0 Hz), 5.219 (dd, 1H, H-4, $J_{H-4,H-5}$=$J_{H-4,H-3}$=9.7 Hz), 5.39 (dd, 1H, H-3, $J_{H-3,H-2}$=9.4 Hz).

4'(N-Oxysuccinimidylcarbonyl)Butyl 2,3,4,6-Tetra-O-(3-Perfluorooctyl)Propionyl-β-D-Glucopyranoside 8

In a 100-mL round-bottom flask equipped with magnetic stirring bar, nitrogen inlet, and bent-tube adapter were placed 7 (1.985 g, 0.91 mmol), powdered molecular sieves 4Å (50 mg), dimethylaminopyridine (167 mg, 1.36 mmol), N-hydroxysuccinimide (156 mg, 1.36 mmol), acetone (10 mL) and Freon®-113 (1,1,2-trichlorotrifluoroethane, 15 mL) and stirred at 0° C. To the above mixture was added dicyclohexylcarbodiimide (309 mg, 1.5 mmol) in acetone (5 mL). The contents were then allowed to warm up to room temperature and further stirred for 3 h. The reaction mixture was then filtered and the residue after removal of solvent was chromatographed (silica gel 70 g, 1:5 ethyl acetate/Freon®-113) to provide 8 (902 mg, 43.6%). The reaction is almost quantitative by TLC (thin layer chromatography). However, the yield varies from experiment to experiment due to instability of 8 during chromatography.

$^1$H NMR (300 MHz, CDCl$_3$+Freon®-113) δ0.8–2.0 (m,g 4H, H-2+H-3'), 2.593 (m, 18H, H-4'+4×—COCH$_2$CH$_2$CF$_2$—), 2.807 (s, 4H, succinimidyl Hs), 3.595 (m, 1H, H-1'A), 3.748 (m, 1H, H-5), 3.926 (m, 1H, H-1'B), 4.182 (dd, 1H, H-6A, $J_{H-6A,H-6B}$=11.1 Hz, $J_{H-6A,5}$=1.7 Hz), 4.467 (dd, 1H, H-6B, $J_{H-6A,H-6B}$=12.5 Hz, $J_{6B,H5}$=3.9 Hz), 4.591 (d, 1H, H-1, $J_{H-1,H-2}$=8.0 Hz), 5.082 (dd, 1H, H-2, $J_{H2,H3}$=$J_{H2,H1}$=8.7 Hz), 5.188 (dd, 1H, H-4, $J_{H4,H3}$=$J_{H4,H5}$=9.6 Hz), 5.290 (dd, 1H, H-3, $J_{H3,H4}$=$J_{H3,H2}$=9.3 Hz).

4'-Oxopentyl 2,3,4,6-Tetra-O-(3-Perfluorooctyl)Propionyl-β-D-Glucopyranoside 9

In a 50-mL round-bottom flask with a magnetic stirrer bar, bent-tube adapter and gas inlet was placed 6 (0.5 g, 0.23 mmol) in dichloromethane (5 mL) and Freon®-113 (10 mL). The resulting solution was cooled to 0° C. and ozone was passed through the solution for 20 min, the excess ozone flushed out by passing nitrogen and the ozonide decomposed by the addition of thiourea (454 mg, 0.6 mmol) in methanol (10 mL) and stirred for 1 h at room temperature. The contents were diluted with water (100 mL) and extracted with Freon®-113. The organic extract was dried and residue after removal of solvent chromatographed (silica gel 30 g, 1:10 ethyl acetate/Freon®-113), to provide 9 (110 mg, 21% yield).

$^1$H NMR (300 MHz; CDCl$_3$+Freon®-113) δ1.622 (m, 4 H, H-2'+H-3'), 2.606 (m, 18H, —COCH$_2$CH$_2$CF$_2$—+H-4'), 3.519 (m, 1H, H-1'A), 3.731 (m, 1H, H-5), 3.905 (m, 1 H, H'-1B) 4.186 (br d, 1H, H-6A, $J_{H-6A,H-6B}$=11.8 Hz), 4.461 (dd, 1H, H-6B, $J_{H-6B,H-6A}$=12.5 Hz, $J_{H-6B,H-5}$=4.0 Hz), 4.542 (d, 1H, H-1, $J_{H-1,H-2}$=8.0 Hz), 5.07 (dd, 1 H, H-2, $J_{H-1,H-2}$=$J_{H-2,H-3}$=8.6 Hz), 5.178 (dd, 1H, H-4, $J_{H-4,H-3}$=$J_{H-4,H-5}$=9.5 Hz), 5.285 (dd, 1H, H-3, $J_{H-3,H-4}$=$J_{H-3,H-2}$=9.3 Hz), 9.58 (s, 1H, CHO).

5',6'-Epoxyhexyl 2,3,4,6-Tetra-O-(3-Perfluorooctyl)Propionyl-β-D-Glucopyranoside 10

In a 100-mL round-bottom flask equipped with magnetic stirring bar, nitrogen inlet and bent-tube adapter was placed 6 (3.1 g, 1.44 mmol) in a mixture of dichloromethane (18 mL) and Freon®-113 (18 mL) and m-chloroperbenzoic acid (m-CPBA) (85%, 0.65 g, 3.19 mmol). The contents were stirred at room temperature for 4 h. The reaction was incomplete. An additional amount (0.65 g) of m-CPBA was added, and the contents stirred at room temperature for 18 h. The reaction mixture was cooled to 0° C., and the excess m-CPBA was decomposed by the addition of sodium sulfite (5.17 g, 41 mmol) in water (15 mL). The contents were further stirred for 30 min, extracted with a mixture of Freon®-113 and dichloromethane, and the residue chromatographed (silica gel 90 g, 1:10 ethyl acetate/Freon®-113) to provide 10 (2.4 g, 77% yield).

$^1$H NMR (300 MHz; CDCl$_3$+Freon®-113) δ1.496–1.622 (m, 6H, H-2', H-3', H-4'), 2.606 (m, 18H, —OCOCH$_2$CH$_2$CF$_2$—, H-6'), 2.859 (m, 1H, H-5'), 3.519 (m, 1H, H-1'A), 3.731 (m, 1H, H-5), 3.905 (m, 1H, H-1'B), 4.186 (br d, 1H, H-6A, $J_{H\text{-}6A,H\text{-}6B}$=11.8 Hz), 4.461 (dd, 1H, H-6B, $J_{H\text{-}6B,H\text{-}6A}$=12.5 Hz, $J_{H\text{-}6B,H\text{-}5}$=4.0 Hz), 4.542 (d, 1H, H-1, $J_{H\text{-}1,H\text{-}2}$=8.0 Hz), 5.070 (dd, 1H, H-2, $J_{H\text{-}1,H\text{-}2}$=$J_{H\text{-}2,H\text{-}3}$=8.6 Hz), 5.178 (dd, 1H, H-4, $J_{H\text{-}4,H\text{-}3}$=$J_{H\text{-}4,H\text{-}5}$=9.5 Hz), 5.285 (dd, 1H, H-3, $J_{H\text{-}3,H\text{-}4}$=$J_{H\text{-}2,H\text{-}3}$=9.3 Hz).

$^{13}$NMR (75 MHz; CDCl$_3$+Freon®-113) δ22.798, 22.822 (C-3') 29.342, 29.392 (C-2'), 32.277, 32.291 (C-4'), 46.734 (C-6'), 52.031, 52.065 (C-5'), 62.232 (C-6), 68.985, 70.006, 70.251, 72.181, 72.350, 73.902, 77.201 (C-2, C-3, C-4, C-5, C-1'), 101.043, 101.090 (C-1), 169.936, 170.298, 170.836, 171.104. (The compound is a mixture of diastereoisomers at C-5'.)

IR (nujol) 1755 (OCOR), 1250–1150 (CF$_2$).

5'-Hydrazinocarbonylpentyl 2,3,4,6-Tetra-O-(3-Perfluorooctyl)Propionyl-β-D-Glucopyranoside 11

In a 200-mL round-bottom flask equipped with reflux condenser, magnetic stirring bar and inlet were placed under oxygen and moisture-free conditions compound 8 (1.5 g, 0.66 mmol), Freon®-113 (37.5 mL), trifluoroethanol (37.5 mL; trifluoroethanol is a reproductive toxin), and cooled to 0° C. Anhydrous hydrazine (0.105 mL), was added slowly and the contents allowed to warm up to room temperature and stirred for 3 h. (TLC 1:5 ethyl acetate/Freon®-113). The contents were made free of solvents and the residue chromatographed (silica gel 80 g, 10% trifluoroethanol in Freon®-113) to provide 11 (1.00 g, 69.8% yield).

$^1$H NMR (300 MHz; CDCl$_3$+Freon®-113) δ0.85–2.05 (m, 4.0H, H-2', H-3'), 2.160 (m, 1H, H-4'), 2.573 (m, 16H, —OCOCH$_2$CH$_2$CF$_2$—), 3.537 (m, 1H, H-1'A), 3.733 (m, 1H, H-5), 3.909 (m, 1H, H-1'B), 4.213 (br d, 1H, H-6A, $J_{H\text{-}6A,H\text{-}6B}$=10.9 Hz), 4.47 (dd, 1H, H-6B, $J_{H\text{-}6B,H\text{-}6A}$=12.6 Hz, $J_{H\text{-}6B,H\text{-}5}$=4.0 Hz), 4.53 (d, 1H, H-1, $J_{H\text{-}1,H\text{-}2}$=8.0 Hz), 5.093 (dd, 1H, H-2, $J_{H\text{-}2,H\text{-}3}$=$J_{H\text{-}2,H\text{-}1}$=8.6 Hz), 5.187 (dd, 1H, H-4, $J_{H\text{-}4,H\text{-}5}$=9.6 Hz), 5.299 (dd, 1H, H-3, $J_{H\text{-}3,H\text{-}4}$=$J_{H\text{-}3,H\text{-}2}$=9.3 Hz).

$^{13}$C NMR (75 MHz; CDCl$_3$+Freon®-113) δ22.010, (C-3'), 28.322 (C-2'), 33.312 (C-4'), 61.652 (C-6), 69.620, 71.126, 71.839, 73.314, (C-1', C-2, C-3, C-4, C-5), 100.640 (C-1), 169.765, 169.810, 170.281, 170.635, 173.149 (4×—OCOCH$_2$CH$_2$, CONHNH$_2$).

IR (KBr) 3340 (NH-NH$_2$), 1750 (—OCOCH$_2$—), 1655, 1250–1200 (CF$_2$).

FAB MS calcd for C$_{55}$H$_{34}$F$_{68}$N$_2$O$_{11}$ (M+H) 2191.11. Found 2190.20.

5'-(N-Benzyloxycarbonyl)Aminopentanol 13

In a 500-mL round-bottom flask equipped with magnetic stirring bar, bent-tube adapter and nitrogen inlet were placed N-benzyloxycarbonylsuccinimide (23.3 g, 93.5 mmol), absolute ethyl alcohol (250 mL) and 5-aminopentanol 12 (9.65 g, 93.5 mmol). The contents were stirred at room temperature for 3 h. The solvent was removed and the residue chromatographed (silica gel 325 g, 20:1:20 ethyl acetate/ethyl alcohol/hexane) to provide 13 (14.053 g, 63.3%).

$^1$H NMR (300 MHz; CDCl$_3$) δ1.401 (m, 2H, H-3), 1.557 (m, 4H, H-2, H-4), 1.743 (s, 1H, OH), 3.203 (q, 2H, H-5, J=6.6 Hz), 3.632 (q, 2H, H-1, J=5.8 Hz), 4.826 (br s, 1H, NH), 5.089 (s, 2H, —OCH$_2$Ph), 7.350 (s, 5H, aromatic).

$^{13}$C NMR (75 MHz; CDCl$_3$) δ22.889 (C-3), 29.750 (C-4), 32.215 (C-2), 40.96 (C-5), 62.553 (C-1), 66.593 (OCH$_2$Ph), 127.987, 128.425, 136.621 (aromatic carbons), 156.442 (OCOO).

IR (KBr) 3400 (—NH—), 3340 (—OH), 1690 (—NH-COO), 1535, 1260, 1020.

FAB MS calcd for C$_{13}$H$_{19}$NO$_3$ (M+H) 238.14. Found 238.08.

5'-(N-Benzyloxycarbonyl)Aminopentyl 2,3,4,6-Tetra-O-Acetyl-β-D-Glucopyranoside 14

In a 1-liter round-bottom flask equipped with an overhead mechanical stirrer, reflux condenser and addition funnel were placed 13 (14.053 g, 59 mmol), silver carbonate (16.54 g, 60 mmol), calcium sulfate (10 g) and dichloromethane (200 mL). The vigorously stirred solution was added 3 (12.3 g, 30 mmol) in 100 mL of dichloromethane over a 2 h period. The mixture was further stirred for 40 h at room temperature, filtered through a Celite pad and the residue after removal of solvent was dissolved in a mixture (1:1) of toluene and nitromethane (200 mL). To the above solution was added 500 mg of mercuric bromide and the contents were heated at 50° (bath) over a 24 h period. The solvent was removed, residue dissolved in dichloromethane and the organic extract washed with sodium thiosulfate. The organic extract after drying and removal of solvent was chromatographed (silica gel 500 g, 2:3 ethyl acetate/hexane) to provide 14 (5.849 g, 34.4%).

$^1$H NMR (300 MHz, CDCl$_3$) δ1.355 (m, 2H, H-3') 1.507 (m, 1H, H-4'), 1.586 (m, 1H, H-2'), 2.003, 2.024, 2.024, 2.078 (4 s, 12H, 4×OCOCH$_3$), 3.176 (br q, 2H, H-5', J=6.6 Hz), 3.474 (m, 1H, H-1'A), 3.68 (m, 1H, H-5), 3.86 (m, 1H, H-1B), 4.138 (dd, 1H, H-6A), J$_{H\text{-}6A,H\text{-}6B}$=12.3 Hz, $J_{H\text{-}6A,H\text{-}5}$=2.4 Hz), 4.258 (dd, 1H, H-6B, $J_{H\text{-}6B,H\text{-}6A}$=12.3 Hz, $J_{H\text{-}6B,H\text{-}5}$=4.7 Hz), 4.479 (d, 1H, H-1, $J_{H\text{-}1,H\text{-}2}$=7.9 Hz), 4,841 (m, 1H, —NH—), 4.975 (dd, 1H, H-2, $J_{H\text{-}2,H\text{-}3}$=9.4 Hz, $J_{H\text{-}1,H\text{-}2}$=8.0 Hz), 5.079 (dd, 1H, H-4, $J_{H\text{-}3,H\text{-}4}$=$J_{H\text{-}4,H\text{-}5}$=9.6 Hz), 5.088 (s, 1H, —OCH$_2$Ph), 5.200 (dd, 1H, H-3, $J_{H\text{-}2,H\text{-}3}$=$J_{H\text{-}3,H\text{-}4}$=9.4 Hz), 7.347 (s, 5H, aromatic).

$^{13}$C NMR (75 MHz, CDCl$_3$) δ20.545, 20.655 (OCOCH$_3$), 23.072 (C-3'), 28.986 (C-4'), 29.594 (C-2'), 40.976 (C-5'), 62.043 (C-6'), 66.575 (—OCH$_2$Ph), 68.642, 69.692, 71.456, 71.864, 72.92 (C-1', C-2, C-3, C-4, C-5), 100.762 (C-1), 127.993, 128.436, 136.621 (aromatic), 156.349 (—NHCOO—), 169.161, 169.266, 170.121, 170.490 (4×—OCOCH$_3$).

IR (KBr) 3350 (—NH—), 1750 (—OCOCH₃), 1730, 1685 (—NHCOO—), 1540, 1250-1220, 1050, 1030.

FAB MS calcd for $C_{27}H_{37}NO_{12}$ (M+H) 568.24. Found 568.10.

5'-(N-Benzyloxycarbonyl)Aminopentyl β-D-Glucopyranoside 15

In a 300-mL round-bottom flask equipped with magnetic stirrer bar, septum inlet and bent-tube adapter were placed 14 (3.913 g, 6.89 mmol), methanol (dry; 150 mL) and 0.5N sodium methoxide (2.5 mL) in methanol. The pH of the solution should be >10. The contents were stirred for 3 h (TLC 14:4:1 ethyl acetate/ethyl alcohol/water indicated completion of the reaction). The mixture was neutralized with 1 g of Bio-Rad H+ ion exchange resin AG-50W-X8 and stirred for 10 min. The mixture was filtered and washed with methanol. The filtrate was taken to dryness to provide 15 (2.521 g, 91.5% yield).

¹H NMR (300 MHz; D₂O) δ1.092 (m, 2H, H-3'), 1.232 (m, 2H, H-4'), 1.346 (m, 2H, H-2'), 2,850 (br t, 2H), 2.972 (t, 1H), 3.125 (m, 3H), 3.406 (m, 2H), 3.611 (m, 2H), (H-2, H-3, H-4, H-5, H-6, H-1', H-5'), 4.154 (d, 1H, H-1, $J_{H-1,H-2}$=7.9 Hz), 4.83 (s, 2H, —OCH₂Ph), 7.146 (s, 5H, aromatic).

¹³C NMR (75 MHz; D₂O) δ22.296 (C-3'), 28.408 (C-4'), 28.610 (C-2'), 40.456 (C-5'), 60.907 (C-6), 66.646 (—OCH₂Ph), 69.754, 69.754, 70.213, 73.187, 75.871 (C-2, C-3, C-4, C-5, C-1'), 102.224 (C-1), 127.554, 128.159, 128.625, 136.542 (aromatic), 158.095 (—NHCOO—).

IR (KBr) 3320 (-OH,NH-), 1685 (-NHCOO-), 1540, 1260 (C—O), 1030 (C—O).

FAB MS calcd for $C_{19}H_{29}NO_8$ (M+H) 400.20. Found 400.03.

5'-(N-Benzyloxycarbonyl)Aminopentyl 2,3,4,6-Tetra-O-(3-Perfluorooctyl)Propionyl-β-D-Glucopyranoside 16

In a 100-mL round-bottom flask equipped with a magnetic stirrer bar, septum inlet and bent-tube adapter were placed 15 (600 mg, 1.5 mmol), molecular sieves 4 Å (150 mg), dimethylaminopyridine (911 mg, 7.5 mmol), perfluorooctylpropionic acid (4.69 g, 7.5 mmol), anhydrous dimethyl formamide (2.5 mL) and anhydrous Freon®-113 (7.5 mL). The above mixture was stirred at 0° C. and dicyclohexylcarbodiimide (1.857 g, 9 mmol) in 5 mL of anhydrous dimethylformamide was added to the above mixture. The contents were then stirred at room temperature for 20 h. The reaction mixture was filtered, washed with 1:1 Freon®-113/dichloromethane mixture (3×50 mL) and the filtrate concentrated. The residue after solvent removal was chromatographed (silica gel 200 g, 1:5 ethyl acetate/Freon®-113 to provide 16 (2.984 g, 86.6% yield).

¹H NMR (300 MHz; CDCl₃+Freon®-113) δ1.401 (m, 2 H, H-3'), 1.527 (m, 2H, H-4'), 1.617 (m, 2H, H-2'), 2.541 (m, 16H, —OCOCH₂CH₂(CF₂)₇CF₃), 3.198 (br q; 2H, H-5', J=6.6 Hz), 3.509 (m, 1H, H-1'A), 3.719 (br d, 1 H, H-5), 3.88 (m, 1H, H-1'B), 4.185 (br d, 1H, H-6A, $J_{H-6A,H-6B}$=11.1 Hz), 4.471 (dd, 1H, H-6B, $J_{H-6B,H-6A}$=12.4 Hz, $J_{H-6B,H-5}$=3.8 Hz), 4.530 (d, 1H, H-1, $J_{H-1,H-2}$=8.0 Hz), 4.733 (m, 1H, -NH-), 5.066 (dd, 1H, H-2, $J_{H-2,H-3}$=$J_{H-1,H-2}$=9.0 Hz), 5.096 (s, 2H, —OCH₂Ph), 5.179 (dd, 1H, H-4, $J_{H-4,H-3}$=$J_{H-4,H-5}$=9.6 Hz), 5.284 (dd, 1H, H-3, $J_{H-3,H-4}$=$J_{H-3,H-2}$=9.4 Hz), 7.337 (s, 5H, aromatic).

¹³C NMR (300 MHz; CDCl₃+Freon®-113) δ22.932, (C-3'), 28.895 (C-4'), 29.590 (C-2'), 40.811 (C-5'), 1.994 (C-6), 66.622 (-OCH₂Ph), 68.558, 69.956, 71.611, 71.890, 73.383 (C-2, C-3, C-4, C-5, C-1'), 100.547 (C-1), 127.554, 128.498, 136.556 (aromatic), 158.095 (—NHCOO—), 169.936, 170.298, 170.836, 171.104 (4×—OCOCH₂CH₂CF₂—).

IR (KBr) 3380 (—NH—), 1755 (—OCOCH₂), 1695 (—NHCOO—), 1540, 1250-1200, (—C—O—CF—), 1150 (C—O).

FAB MS calcd for $C_{63}H_{41}F_{68}NO_{12}$ (M+H) 2296.16. Found 2296.00.

5'-Aminopentyl 2,3,4,6-Tetra-O-(3-Perfluorooctyl)-Propionyl-β-D-Glucopyranoside 17

In a 50-mL round-bottom flask equipped with magnetic stirrer bar, septum inlet and bent-tube adapter were placed 16 (229 mg, 0.1 mmol), palladium black (50 mg), trifluoroethanol (2 mL) and Freon®-113 (18 mL) and stirred at room temperature. The mixture was then exposed to hydrogen using hydrogen balloon for 3 h. At this point, the reaction was complete (TLC 10% methanol in Freon®-113). The reaction mixture was filtered through a Celite pad and the filtrate concentrated to provide 17 (204 mg, 94% yield).

¹H NMR (300 MHz; CF₃CD₂OD+Freon®-113) δ1.376 f(m, 2H, H-3'), 1.595 (m, 2H, H-4'), 1.660 (m, 2H, H-2'), 2.566 (m, 16H, OCOCH₂CH₂CF₂—), 2.937 (br s, 2H, H-5'), 3.540 (m, 1H, H-1'A), 3.815 (m, 1H, H-1'B), 4.207 (d, 1H, H-6A, $J_{H-6A,H-6B}$=12.1 Hz), 4.318 (d, 1H, H-6B, $J_{H-6B,H-6A}$=12.0 Hz), 4.513 (d, 1H, $J_{H-1,H-2}$=6.9 Hz), 4.513 (d, 1H, H-1, $J_{H-1,H-2}$=8.2 Hz), 4.967 (dd, 1H, H-2, $J_{H-2,H-3}$=$J_{H-1,H-2}$=8.2 Hz), 5.139 (dd, 1H, H-4, $J_{H-4,H-3}$=$J_{H-4,H-5}$=8.6 Hz), 5.273 (dd, 1H, H-3, $J_{H-3,H-4}$=$J_{H-3,H-2}$=9.3 Hz).

IR (KBr) 3420 (—NH₂), 1750 (—OCOCH₂—), 1250-1200 (—CF—), 1150 (C—O).

FAB MS calcd for $C_{55}H_{35}F_{68}NO_{10}$ (M+H) 2162.12. Found 2162.32.

4-Pentenylamine (19)

A mixture of lithium aluminum hydride (10.3 g, 13.6 mmol) and diethyl ether (500 mL) were cooled to ~5° C. (ice-bath) To the above stirred suspension was added slowly a solution of 4-pentenenitrile (11.0 g, 136 mmol) in 50 mL anhydrous ether. The reaction mixture was allowed to warm up to room temperature and further stirred for 2 h. The excess reagent was quenched with sodium sulfate (solid), filtered, dried over sodium sulfate and filtered again. The filtrate was distilled through a Vigreaux column to give 7.16 g of 19 as colorless liquid, bp 107°-111° C.

¹H NMR (300 MHz; CDCl₃) δ1.433 (s, 2H, NH₂), 1.548 (quint, 2H, H-2, J=7.3 Hz), 2.099 (quart, 2H, H-3, J=6.9 Hz), 2.709 (t, 2H, H-1, J=7.1 Hz), 4.996 (m, 2H, H-5), 5.819 (m, 1H, H-4).

IR (NaCl) 3280 (NH₂), 1640 (CH=CH₂) cm⁻¹.

N-4'-Pentenyl Gluconamide 20

Gluconolactone (18) (1.34 g, 7.5 mmol), 4-pentenylamine (0.85 g, 10 mmol), acetonitrile (34 mL) and water (11 mL) were combined and heated at 60° for 2 h. The mixture was made free of solvent, residue dissolved in water and lyophilized to give 1.94 g of 20. The crude product was treated with pyridine (29.8 mL, 369 mmol) and acetic anhydride (17.4 mL, 185 mmol) and stirred at room temperature for 18 h. It was poured into mixture of water and ice and then extracted with dichloromethane (3×50 mL). The combined dichloromethane layer was washed with 1 N HCl (150 mL, ice-cold), 50 mL of saturated sodium bicarbonate, 50 mL of brine and then dried over magnesium sulfate. The residue after filtration and removal of solvent furnished 2.35 g, 71% yield, of pure 21 after flash chromatography (silica gel 130 g, 1:2 ethyl acetate/hexane).

$^1$H NMR (CDCl$_3$) δ1.602 (quint, 2H, H-2', J=7.3 Hz), 2.057 (s, 3H, OCOCH$_3$), 2.098 (s, 3H, -OCOCH$_3$), 2.117 (s, 3H, —OCOCH$_3$), 2.209 (s, 3H, —OCOCH$_3$), 2.2 (m, 2H, H-3'), 3.276 (br q, 2H, H-1', J=6.2 Hz), 4.131 (dd, 1H, H-6A, $J_{H-6A,H-5}$=5.4 Hz, $J_{H-6A,H-6B}$=12.2 Hz), 4.319 (dd, 1H, H-6B, $J_{H-6B,H-5}$=4.0 Hz, $J_{H-6B,H-6A}$=12.3 Hz), 5.010 (m, 2H, H-5'), 5.065 (m, 1H, H-5), 5.292 (d, 1H, H-2, $J_{H-2,H-3}$=5.5 Hz), 5.447 (dd, 1H, H-4, $J_{H-4,H-3}$=5.0 Hz, $J_{H-4,H-5}$=6.4 Hz), 5.684 (dd, 1 H, H-3, $J_{H-3,H-2}$=5.2 Hz, $J_{H-3,H-4}$=5.2 Hz), 5.788 (m, 1 H, H-4'), 6.134 (br t, 1H, NH).

$^{13}$C NMR (75 MHz, CDCl$_3$) 20.245, 20.477 (OCOCH$_3$), 28.400 (C-2'), 30.840 (C-3'), 38.923 (C-1'), 61.462 (C-6), 68.779 (C-5), 69.022 (C-3), 69.388 (C-4), 71.600 (C-2), 115.218 (C-5'), 137.359 (C-4').

IR (KBr) 3360, 3250 (—NH), 1750 (—COCH$_3$), 1660, 1670 (—CONH—), 1530 (—CONH—), 1220 (ester) cm$^{-1}$.

Pentaacetate 21 was saponified as follows: the pentacetate 21 (2.11 g, 4.5 mmol) was dissolved in 45 mL of dry methanol and treated with sodium methoxide (0.45 mL, 0.5 M) and stirred at room temperature for 1 h. To the mixture was then added acidic resin AG-50W-X8 (0.94 g) and stirred for 10 min. The mixture was filtered and evaporated to provide 20 (1.21 g, 72% overall yield) as white solid.

$^1$H NMR (D$_2$O) δ1.615 (quint, 2H, H-2', J=7.3 Hz), 2.077 (q, 2H, H-3', J=7.2 Hz), 3.243 (t, 2H, H-1', J=6.9 Hz), 3.715-4.044 (m, 4H, H-3, H-4, H-5, H-6A, H-6B), 4.272 (d, 1H, H-2, $J_{H-2,H-3}$=3.6 Hz), 5.035 (m, 2H, H-5'), 5.874 (m, 1H, H-4').

$^{13}$C NMR (D$_2$O) ($^1$H decoupled) δ27.671 (C-2'), 30.295 (H-3'), 38.694 (H-1'), 62.842, 70.549, 71.455, 72.247, 73.441 (C-2, C-3, C-4, C-5, C-6), 114.857 (C-5'), 138.924 (C-4'), 173.848 (C-1).

IR (KBr) 3320 (OH), 1650 (—CONH—), 1540 (—CONH—)cm$^{-1}$.

N-4'-Pentenyl 2,3,4,5,6-Penta-O-(3-Perfluorooctyl)Propionyl Gluconamide 22

In a 100-mL round-bottom flask were placed compound 20 (0.26 g, 1 mmol), powdered molecular sieves (0.4 g), N,N-dimethylaminopyridine (0.76 g, 6.3 mmol), perfluorooctylpropionic acid (3.1 g, 6.3 mmol), anhydrous dimethylformamide (5 mL), and Freon ®-113 (15 mL) and cooled to ~0° C. To the above mixture was added dicyclohexylcarbodiimide (1.6 g, 7.5 mmol) in 10 mL of Freon ®-113 and stirred for 18 h at room temperature. The mixture was filtered and the residue after removal of solvent was chromatographed (silica gel, 1:10, ethyl acetate/Freon ®-113) to provide 22 as white solid (3.11 g).

$^1$H NMR (300 MHz; CDCl$_3$+Freon ®-113 1:1) δ1.05-2.15 (m, 27H, expected 4H, H-2', H-3' and impurity), 2.613 (m, 27H, expected 20H, —COCH$_2$CH$_2$—C$_8$F$_{17}$), 3.725 (m, 1.2H impurity), 3.967 (m, 1.3H, impurity), 4.22 (dd, 1H, H-6A, $J_{H-6A,H-6B}$=12.4 Hz, $J_{H-6A,H-5}$=6.0 Hz), 4.466 (dd, 1H, H-6B, $J_{H-6B,H-6A}$=12.3 Hz, $J_{H-6B,H-5}$=3.3 Hz), 5.01 (m, 2H, H-5'), 5.115 (m, 1H, H-5), 5.406 (d, 1H, H-2, $J_{H-2,H-3}$=5.3 Hz), 5.532 (t, 1H, J=5.7 Hz), 5.784 (m, 2H, H-3 and H-4'), 6.105 (br t, 1H, NH).

IR (KBr) 3440 (NH), 1750 (—COO—), 1650 (—CONH—), 1540 (—CONH—), 1200 (CF) cm$^{-1}$.

FAB MS m/e (M+H) calcd for C$_{66}$H$_{36}$NO$_{11}$F$_{85}$ 2634.9. Found 2634.8.

N-(4',5'-Epoxy)Pentyl 2,3,4,5,6-Penta-O-(3-Perfluorooctyl-Propionyl) Gluconamide 23

In a 250-mL round-bottom flask equipped with magnetic stirring bar and bent-tube adapter were placed compound 22 ((3.0 g, 1.13 mmol), dichloromethane (50 mL), Freon ®-113 (50 mL), and m-chloroperbenzoic acid (1.15 g, 85%, 5.65 mmol) and stirred at room temperature for 18 h. It was then cooled to ~5° C. and slowly treated with sodium sulfite (9.63 g in 52 mL of water) and further stirred for 0.5 h. It was then taken up in a separatory funnel and washed successively with cold saturated sodium bicarbonate, cold brine and the organic extract after drying removal of solvent was chromatographed (silica gel 1:7 ethyl acetate/Freon ®-113) to provide 23 (2.5 g, 85% yield) as white solid.

$^1$H NMR (300 MHz; CDCl$_3$, Freon ®-113 1:1) δ0.8-2.2 (m, 4H, H-2', H-3'), 2.719 (m, 23H, —OCOCH$_2$CH$_2$(CF$_2$)CF$_3$, H-4', H-5'), 3.16, 3.322, 3.473, 3.62 (4 m, 2H, H-1'), 4.25 (dd, 1H, H-6A, $J_{H-6A,H-6B}$=12.3 Hz, $J_{H-6A,H-5}$=6.3 Hz), 4.507 (br d, 1H, H-6B, J=8.8 Hz), 5.143 (br q, 1H, H-5), 5.469 (d, 0.5H, H-2A, $J_{H-2A,H-3}$=4.8 Hz), 5.495 (d, 0.5H, H-2B, $J_{H-2B,H-3}$=4.8 Hz), 5.588 (t, 1H, H-4, J=5.7 Hz), 5.830 (t, 1H, H-3, J=5.3 Hz), 6.790-6.969 (2 br t, 1 H, NH).

IR (KBr) 1750 (ester), 1670 (amide I), 1540 (amide II), 1200 (CF) cm$^{-1}$.

FAB MS m/e (M+H) calcd for C$_{66}$H$_{36}$NO$_{12}$F$_{85}$ 2650.9. Found 2651.6.

N-3'-Carboxypropyl 2,3,4,5,6-Penta-O-(3-Perfluorooctyl)Propionyl Gluconamide 24

In a 100-mL round-bottom flask compound 22 (1.32 g, 0.5 mmol), sodium metaperiodate (0.21 g, 1.0 mmol), periodic acid (0.23 g, 1 mmol), ruthenium tetroxide (5 mg), Freon ®-113 (7 mL), acetonitrile (7 mL), and water (9 mL) were combined and stirred for 2 h at room temperature. The reaction mixture was filtered and washed with Freon ®-113. The combined organic layer was washed with 20 mL of brine, dried over magnesium sulfate and the filtrate after removal of solvent furnished 24 (1.31 g, 99% crude).

$^1$H NMR (300 MHz; Acetone-d$_6$, Freon ®-113) δ1.0-2.1 (m, 26H, expected 2H, H-2 impurity), 2.303 (t, 2H, H-3', J=7.2 Hz), 2.69 (m, 27H, expected 20H, —OCOCH$_2$CH$_2$(CF$_2$)$_7$CF$_3$, 3.236 (m, 2H, H-1'), 3.638 (m, 1.2 H, imp), 4.013 (m, 1.2H, impurity), 4.313 (dd, 1H, H-6A, J=12.2 Hz, $J_{H-6A,H-5}$=6.3 Hz), 4.506 (dd, 1H, H-6B, $J_{H-6B,H-6A}$=12.2 Hz, $J_{H-6B,H-5}$=4.0 Hz), 5.226 (br q, 1H, H-5), 5.416 (d, 1H, H-2, $J_{H-2,H-3}$=4.6 Hz), 5.612 (t, 1H, H-4, J=5.6 Hz), 5.824 (m, 1H, H-3), 7.438 (br d, 1H, impurity), 7.595 (br t, 1H, NH).

IR (KBr) 3340 (NH), 1750 (—COO—), 1680, 1660 (amide I), 1530 (amide II), 1200 (CF) cm$^{-1}$.

N-3'-(N-Oxysuccinimidylcarbonyl)Propyl 2,3,4,5,6-Penta-O-(3-Perfluorooctyl)Propionyl Gluconamide 25

In a 100-mL round-bottom flask were placed compound 24 (1.0 g, 0.38 mmol), powdered dry 4 Å molecular sieves (50 mg), dimethylaminopyridine (122 mg, 1.0 mmol), N-hydroxysuccinimide (116 mg, 1.0 mmol), acetone (7.5 mL) and Freon ®-113 (7.5 mL) and stirred at ~5° C. To the above mixture was added dicyclohexylcarbodiimide (240 mg, 1.16 mmol) and the resulting mixture was stirred at room temperature for 18 h. Dimethylanimopyridine, N-hydroxy succinimidyl ester and dicyclohexylcarbodiimide were again added in the same amount as before and stirred for 3 h at room temperature. The reaction mixture was then filtered, concentrated and purified by flash chromatography (silica gel, 1:3 ethyl acetate/Freon ®-113) to give 25 (0.29, 28% yield) as white solid.

$^1$H NMR (300 MHz; CDCl$_3$, Freon ®-113 1:1) δ2.050 (t, 2H, H-2'), 2.651 (m, 26H, H-3', —COCH$_2$CH$_2$CF$_2$— and —COCH$_2$CH$_2$CH$_2$COON ), 3.345–3.485 (m, 2H, H-1'), 4.195 (dd, 1H, H-6A, J$_{H-6A,H-6B}$=12.4 Hz, J$_{H-6A,H-5}$=6.2 Hz), 4.438 (dd, 1H, H-6B, J$_{H-6B,H-6A}$=12.4 Hz, J$_{H-6B,H-5}$=3.1 Hz), 5.167 (m, 1H, H-5), 5.343 (d, 1H, H-2, J$_{H-2,H-3}$=6.0 Hz), 5.518 (dd, 1H, H-4, J$_{H-4,H-3}$=4.6 Hz, J$_{H-4,H-5}$=6.6 Hz), 5.728 (dd, 1H, H-3, J=H-3, H-2=5.8 Hz, J$_{H-3,H-4}$=4.7 Hz), 6.85 (br t, 1H, -NH-).

N-4'-Pentenyl Glucoheotanamide 27

In a 250-mL round-bottom flask equipped with magnetic stirrer and bent-tube adapter were placed glucoheptanolactone 26 (3.7 g, 17.7 mmol), 4-pentenylamine 19 (2.0 g, 29.5 mmol), anhydrous dimethylformamide (150 mL) and the mixture was stirred at room temperature for 22 h. The solvent was removed under high vacuum (0.1 mm, 46°–53° C., bath temperature) to provide 10 (5.3 g, ~100% yield) in essentially ~100% purity and it was used without further purification.

$^1$H NMR (D$_2$O) δ1.599 (quint, 2H, H-2', J=7.3 Hz), 2.066 (q, 2H, H-3', J=7.2 Hz), 3.22 (t, 2H, H-1', J=7.0 Hz), 3.59–3.79 (m, 6H, H-3, H-4, H-5, H-6, H-7A, H-7B), 4.204 (d, 1H, H-2, J$_{H-2,H-3}$=5.4 Hz), 4.99 (m, 2H, H-5'), 5.871 (m, 1H, H-4').

IR (KBr) 3330 (—OH), 1650 (amide I), 1540 (amide II) cm$^{-1}$.

The structure of 27 was further confirmed by its conversion into hexaacetate 28.

$^1$H NMR (CDCl$_3$) δ1.651 (quint, 2H, H-2', J=7.3 Hz), 2.022–2.216 (5 s+m, 20 H, 6 OCOCH$_3$, H-3'), 3.350 (m, 2H, H-1'), 4.076 (dd, 1H, H-7A, J$_{H-7A,H-7B}$=12.5 Hz, J$_{H-7A,H-6}$=5.4 Hz), 4.229 (dd, 1H, H-7B, J$_{H-7B,H-7A}$=12.5 Hz, J$_{H-7B,H-6}$=3.0 Hz), 5.027 (m, 2H, H-5'), 5.099 (m, 1H, H-6), 5.235 (d, 1H, H 2, J$_{H-2,H-3}$=3.1 Hz), 5.429 (dd, 1H, H-3, J$_{H-3,H-2}$=3.1 Hz, J$_{H-3,H-4}$=7.8 Hz), 5.815 (m, 3H, H-4, H-5, H-4'), 6.257 (br t, 1H, NH).

$^{13}$C NMR (CDCl$_3$) 20.504, 20.551, 20.627, 20,640, 20.799 (5×OCOCH$_3$), 28.642 (C-2'), 31.009 (C-3'), 38.833 (C-1'), 61.924 (C-7), 68.515 (C-6), 68.874, 69.507 (C-4, C-5), 76.576 (C-2), 76.761 (C-3), 115.404 (C-5'), 137.520 (C-4').

IR (KBr) 1754 (ester), 1680 (amide I), 1540 (amide II), 1220 (CF) cm$^{-1}$.

N-4'-Pentenyl 2,3,4,5,6,7-Hexa-O-(3-Perfluorooctyl)Propionyl Glucoheptanamide 29

In a 100-mL round-bottom flask were placed compound 27 (0.47 g, 1.6 mmol), dimethylaminopyridine (1.5 g, 12 mmol), 4 Å molecular sieves (0.35 g), perfluorooctylpropionic acid (5.9 g, 11.9 mmol), anhydrous dimethylformamide (15 mL), and Freon ®-113 (10 mL) and cooled to ~5° C. To this stirred mixture was added a solution of dicyclohexylcarbodiimide (3.0 g, 14.4 mmol) in 23 mL of Freon ®-113, and the resulting solution was stirred at room temperature for 18 h. The reaction mixture was then filtered, concentrated and chromatographed (silica gel 1:15 ethyl acetate/Freon ®-113 to provide 29 (3.8 g, 77% yield) as white solid.

$^1$H NMR (CDCl$_3$+Freon ®-113 1:1) δ1.661 (quint, 2 H, H-2', J=7.2 Hz), 2.13 (q, 2H, H-3', J=7.1 Hz), 2.626 (m, 24H, —COCH$_2$CH$_2$C$_8$F$_{17}$), 3.377 (m, 2H, H-1'), 4.160 (dd, 1H, H-7A, J$_{H-7A,H-7B}$=12.6 Hz, J$_{H-7A,H-6}$=5.4 Hz), 4.319 (dd, 1H, H-7B, J$_{H-7B,H-7A}$=12.5 Hz, J$_{H-7B,H-6}$=2.4 Hz), 5.027 (m, 2H, H-4'), 5.201 (m, 1H, H-6), 5.257 (d, 1H, H-2, J$_{H-2,H-3}$=2.3 Hz), 5.794 (m, 1H, H-5'), 5.989 (d, 2H, H-4 and H-5, J=8.7 Hz), 6.238 (br t, 1H, NH).

IR (KBr) 1750 (ester, 1680 (amide I), 1540 (amide II), 1200 (CF) cm$^{-1}$.

FAB MS m/e (M+H) calcd for C$_{78}$H$_{41}$NO$_{13}$F$_{102}$ 3139.0. Found 3138.9.

N-(4',5'-Epoxy)-Pentyl 2,3,4,5,6-Hexa-O-(3-Perfluorooctyl)Propionyl Glucoheptanamide 30

In a 50-mL round-bottom flask were placed compound 29 (1.0 g, 0.32 mmol), dichloromethane (8.5 mL), Freon ®-113 (8.5 mL) and cooled to ~5° C. and then m-chloroperbenzoic acid (85%, 0.33 g, 1.6 mmol) was added to the above mixture. The reaction mixture was stirred at room temperature for 18 h. The excess m-chloroperbenzoic acid was decomposed by the addition of sodium sulfite (11.5 g in 63 mL of H20) at ~5 ° C. followed by stirring at room temperature for 0.5 h. The reaction mixture was diluted with 25 mL of dichloromethane and 25 mL of Freon ®-113 and the combined organic extract was washed successively with saturated sodium bicarbonate, brine and then dried over anhydrous sodium sulfate. The extract after filtration followed by removal of solvent and chromatography furnished 30 (silica gel, 1:12 ethyl acetate/Freon ®-113, 0.56 g, 56%) as white solid.

$^1$H NMR (CDCl$_3$/Freon ®, 1:1) δ1.254 (m, 1H, H-2'A, 1.7 (m, 1H, H-2'B), 1.797 (m, 1H, H-3'A), 2.087 (m, 1 H, H-3'B), 2.510 (m, 3.274, 28H, —COCH$_2$CH$_2$C-F$_2$—, H-4', H-5'), 3.274 (m, 1H, H-1'A), 3.561 (m, 1H, H-1B), 4.156 (dd, 1H, H-7A, J$_{H-7A,H-7B}$=12.6 Hz, J=H-7A, H-6=5.5 Hz), 4.323 (dd, 1H, H-7B, J$_{H-7B,H-7A}$=12.8 Hz, J$_{H-7B,H-6}$=2.2 Hz), 5.198 (m, 1H, H-6), 5.256 (d, 0.5H, H-2A, J$_{H-2A,H-2}$=2.3 Hz), 5.264 (d, 0.5H, H-2B, J$_{H-2B,H-3}$=2.3 Hz), 5.508 (m, 1H, H-3), 5.966 (d, 1H, H-4 or H-5, J=6.5 Hz), 5.988 (d, 1H, H-4 or H-5, J=6.7 Hz), 7.013 (br quart, 1H, NH).

IR (KBr) 1750 (ester), 1680 (amide I), 1550 (amide II), 1200 (CF) cm$^{-1}$.

FAB MS m/e (M+H) Calcd for C$_{78}$H$_{41}$NO$_{14}$F$_{102}$ 3155.0. Found 3155.4.

N-3'-Carboxypropyl 2,3,4,5,6,7-Hexa-O-(3-Perfluorooctyl)Propionyl Glucoheptanamide 31

In a 250-mL round-bottom flask equipped with magnetic stirring bar and bent-tube adapter were placed compound 29 (2.6 g, 0.85 mmol), Aliquat® 336 (0.21 g), acetic acid (6.3 mL), hexane (42 mL), Freon® (42 mL) and cooled to ~5° C. in an ice bath. To the above stirred mixture was added potassium permanganate (3.3 g, 20.9 mmol) in 83 mL of water. The reaction mixture was then allowed to stir at room temperature for 18 h. It was cooled to ~5° C. and quenched with sodium sulfite (8.3 g, 66 mmol). After stirring the contents at room temperature for 10 min, the reaction mixture was acidified with 22 mL of 6N HCl. The organic layer was diluted with ether and the aqueous layer was extracted three times with ether/Freon®-113 mixture (6:1). The combined organic extract was washed with brine (50 mL), dried over anhydrous sodium sulfate, filtered and concentrated to provide 31 (2.57 crude, 97.5% yield) as white solid. This was used in the next step without further purification.

N-3'-(N-Oxysuccinimidylcarbonyl)Propyl 2,3,4,5,6,7-Hexa-O-(3-Perfluorooctyl)Propionyl Glucoheptanaide 32

In a 100-mL round-bottom flask equipped with magnetic stirring bar and bent-tube adapter were placed compound 31 (2.57 g, 0.81 mmol), molecular sieves (100 mg), dimethylaminopyridine (122 mg, 1.0 mmol), N-hydroxysuccinimide (105 mg, 1.0 mmol), acetone (25 mL), and Freon®-113 (25 mL) and cooled ~5° C. To the above stirred mixture was added dicyclohexylcarbodiimide (251 mg, 1.22 mmol) and the contents were further stirred for 18 h at room temperature. The mixture was filtered, concentrated and purified by "flash chromatography" to provide 32 (0.418 g, 16% yield) as white solid (silica gel, ethyl acetate/Freon®-113 1:5).

$^1$H NMR (CDCl$_3$/Freon®-113 1:1) δ1.747 (quint, 2H, H-2'), 2.08 (br, quart, 2H, H-3'), 2.616 (m, 28H, —COCH$_2$CH$_2$CF$_2$—, —COCH$_2$CH$_2$CH$_2$CO—), 3.478 (m, 2H, H-1'), 4.167 (dd, 1H, H-7A, $J_{H-7A,H-7B}$=12.7 Hz, $J_{H-7A,H-6}$=5.7 Hz), 4.342 (dd, 1H, H-7B, $J_{H-7BH-7A}$=12.4 Hz, $J_{H-7B,H-6}$=2.1 Hz), 5.208 (m, 1H, H-6), 5.248 (d, 1H, H 2, $J_{H-2,H-3}$=2.5 Hz), 5.528 (dd, 1H, H-3, J=H-3,H-2=2.5 Hz, $J_{H-3,H-4}$=8.5 Hz), 5.981 (m, 2H, H-4 and H-5), 6.396 (br t, 1H, NH).

IR (KBr) 1740 (ester), 1815, 1786 (imide) 1680 (amide I), 1540 (amide II).

Monobenzyloxymethoxyhexaethyleneglycol 34

In a 500-mL round-bottom flask equipped with a magnetic stirring bar were placed 33 (16.4 mL, 65.5 mmol), anhydrous dichloromethane (150 mL), 1,1,3,3-tetramethylurea (15.6 mL, 131 mmol) and stirred at −20° C. To the above mixture was added benzyl chloromethyl ether (9.1 mL, 65.5 mmol). The contents were then stirred at −20° C. for 45 minutes and then allowed to warm up to room temperature and further stirred for 18 h. The mixture was concentrated and chromatographed on silica gel (525 g, 10:2:10 ethyl acetate, ethyl alcohol, hexane) to provide 34 (9.72 g, 37% yield).

$^1$H NMR (300 MHz, CDCl$_3$) δ2.75 (t, 1H, D$_2$O exchange), 3.7 (m, 24H), 4.61 (s, 2H, —OCH$_2$Ph), 4.8 (s, 2H, —OCH$_2$O—), 7.4 (m, 5H, aromatic).

(ω-Benzyloxymethoxy)Pentaethylenoxyethyl 2,3,4,6-Tetra-O-Acetyl-β-D-Glucopyranoside 35

In a 250-mL round-bottom flask equipped with a magnetic stirring bar were placed 34 (4.02 g, 10 mmol), molecular sieves 4 Å (1 g), silver triflate (2.56 g, 10 mmol), and anhydrous nitromethane (50 mL) and cooled to −20° C. To the above mixture was then added collidine (1.3 mL, 10 mmol) and the mixture was further stirred at −20° C. for 15 minutes. Glucosyl bromide 3 (4.92, 11 mmol) was then added and the contents stirred at −20° C. for 18 h. The reaction mixture was diluted with ethyl acetate and filtered through a Celite pad. The filtrate was washed with 10% sodium thiosulfate and brine. The residue was chromatographed on silica gel (200 g, 10:1:10 ethyl acetate, ethyl alcohol, hexane) to provide 35 (724 mg, 10% yield).

$^1$H NMR (300 MHz, CDCl$_3$) δ2.007, 2.025, 2.037, 2.1 (4 s, 3H each, —OCOCH$_3$) 3.68 (m, 24H), 3.9 (m, 1H, H-5), 4.125 (dd, 1H, H-6A), 4.254 (dd, 1H, H-6B), 4.61 (s, 2H, —OCH$_2$Ph), 4.8 (s, 2H, —OCH$_2$O—), 4.86 (d, 1H, H-1), 5.0 (dd, 1H, H-2), 5.09 (dd, 1H, H-4), 5.21 (dd, 1H, H-3), 7.4 (m, 5H, aromatic).

ω-(Benzyloxymethoxy)Pentaethylenoxyethyl β-Glucopyranoside 36

In a 100-mL round-bottom flask equipped with magnetic stirring bar were placed 35 (711 mg, 0.97 mmol), methanol (25 mL), and 0.5N sodium methoxide (0.25 mmol), and stirred at 25° C. for 2 h, and then neutralized with 500 mg of ion exchange resin AG-50W-X8 (Bio-Rad). The contents were stirred for 15 minutes, filtered and solvent removed to provide 36 (525 mg, 96% yield).

$^1$H NMR (300 MHz, D$_2$O), δ3.68 (m, 29H), 4.4 (d, 1 H, H-1), 4.61 (s, 2H, CH$_2$Ph), 4.8 (s, 2H, —OCH$_2$O), 7.4 (s, 5H, aromatic).

(ω-Benzyloxymethoxy)Pentaethylenoxyethyl 2,3,4,6-Tetra-O-(3-Perfluorooctyl)Propionyl-β-D-Glucopyranoside 37

In a 200-mL round-bottom flask equipped with magnetic stirring bar were placed 36 (485 mg, 0.86 mmol), molecular sieves 4 Å (100 mg), perfluorooctylpropionic acid (2.12 g, 4.3 mmol), dimethylaminopyridine (525 mg, 4.3 mmol), Freon®-113 (10 mL), stirred at 0° C. and dicyclohexylcarbodiimide (1.073 g, 5.2 mmol) in 10 mL of dimethylformamide was added. The contents were stirred at room temperature for 18 h. The contents became very thick over the period. It was diluted with Freon®-113 (10 mL) and further stirred for 2 h, filtered, and residue chromatographed on silica gel (130 g, 1:1 ethyl acetate, Freon®-113) to provide 37 (1.493 g, 71% yield).

$^1$H NMR (300 MHz, Freon®-113+CDCl$_3$) δ2.55 (bm, 8H, —CH$_2$CF$_2$—), 3.63 (m, 24H, —OCH$_2$CH$_2$O—), 3.89 (m, 8H, —OCH$_2$CH$_2$CF$_2$), 3.95 (m, 1H, H-5), 4.2 (dd, 1H, H-6A), 4.46 (dd, 1H, H-6B), 4.62 (s, 2H, —OCH$_2$O—), 4.7 (d, 1H, H-1), 5.08 (dd, 1H, H-2), 5.2 (dd, 1H, H-4), 5.32 (dd, 1H, H-3), 7.3 (m, 5H, aromatic).

Pentaethylenoxyethyl 2,3,4,6-Tetra-O-(3-Perfluorooctyl)Propionyl-β-D-Glucopyranoside 38

In a 25-mL round-bottom flask equipped with magnetic stirring bar were placed compound 37 (1.132 g, 0.46 mmol), palladium black (250 mg), Freon®-113 (90 mL) and 2,2,2-trifluoroethanol (18 mL) and stirred under hydrogen atmosphere for 18 h. The mixture was filtered through a Celite pad. The filtrate and washings were combined and the solvent was removed under vacuum to provide 38 (966 mg, 93% yield). The compound was characterized by $^{13}$C NMR.

EXAMPLE 1

Immobilization of Chymotrypsin Using 4'-(N-Oxysuccinimidylcarbonyl)Butyl 2,3,4,6-Tetra-O-(3-Perfluorooctyl)Propionyl-β-D-Glucopyranoside) 8

A one gram sample of fluorocarbon particles was washed with 10 mL of HPLC grade acetone. The particles were then washed twice with 10 mL portions of 1:1 acetone-water. After the washes, the solution above the settled particles was removed with a disposable pipet. Poly(fluoroalkyl) sugar reagent 8 (described on page 21) was dissolved in acetone (2 mg/mL), then enough water was slowly added to give a 1:1 acetone-water mixture. At this point the solution may become slightly cloudy. The reagent solution (10 mL) was added to 1 gram of the washed particles and the suspension was stirred for 30 min to 1 h at room temperature to immobilize the reagent onto the particles. After this time, the particles were washed twice with 10 mL portions of 1:1 acetone-water, followed by four washes with water. During the water washes the particles were stirred gently with a small spatula to prevent the entrapment of air within the particles, which causes them to float.

To immobilize chymotrypsin, 10 mL of a solution of the enzyme (1 mg/mL) in 0.1M, pH 7.5 MOPS buffer was added to the activated particles, and the mixture was stirred for 2 h at room temperature. After immobilization, the particles were washed three times with MOPS buffer. Optionally, the particles were washed twice with 0.2% Zonyl® FSN fluorosurfactant in MOPS buffer for 15 min, followed by three more washes with MOPS buffer.

The amount of chymotrypsin immobilized onto the particles was determined by measuring the amount of protein remaining in the solution after immobilization and in the washes using a colorimetric protein assay.

The activity of chymotrypsin was determined using N-benzoyl-L-tyrosine p-nitroanilide (BTpNA) as substrate. The rate of production of p-nitroaniline was measured at 385 nm. The molar absorption coefficient for p-nitroaniline at this wavelength is $1.258 \times 10^4$. The substrate solution contained nine volumes of 0.04M Tris buffer, pH 8.0, which was 0.005M in calcium chloride and one volume of a solution of BTpNA in acetone (0.00178M). Aliquots of 2.9 mL of the substrate solution were added to 3 mL spectrophotometer cells, 0.1 mL of the diluted (1:10) stock enzyme solution was added, and the absorbance was measured at 2 min intervals for 16 min.

To determine the enzyme activity immobilized on the particles, 50 uL of the settled suspension was added to 2.9 mL of the substrate solution. This mixture was incubated for 10 min at room temperature with vigorous stirring. The suspension was quickly transferred to a dry, preweighed centrifuge tube and centrifuged for 1 min. The supernatant was transferred to a spectrophotometric cell and the absorbance at 385 nm was measured. The remaining particles were quantitatively transferred to the centrifuge tube, washed several times with water, and dried in an oven at 120° C. overnight. The dried particles were weighed the next day to obtain the weight of particles used in the assay. The immobilized enzyme activity per gram of particles and the retention of activity were calculated.

The amount of chymotrypsin immobilized was 9.3 mg per gram of particles. The total enzymatic activity present on the particles was 1.2 IU per gram. The retention of enzymatic activity after immobilization was 33% of the original activity.

EXAMPLE 2

Immobilization of Chymotrypsin Using 3'-(N-Oxysuccinimidylcarbonyl)Propyl 2,3,4,6-Penta-O-(3-Perfluorooctyl)Propionyl Gluconamide 25

The procedure described in Example 1 was used, except that the poly(fluoroalkyl) sugar reagent 25 was substituted for Reagent 8. The amount of chymotrypsin immobilized was 9.1 mg per gram of particles, and the total activity was 1.2 IU per gram of particles. The retention of enzymatic activity after immobilization was 31% of the original activity.

EXAMPLE 3

Immobilization of Chymotrypsin Using N-3'-(N-Oxysuccinimidylcarbonyl)Propyl 2,3,4,5,6,7-Hexa-O-(3-Perfluorooctyl)Propionyl Glucoheptanamide 32

The procedure described in Example 1 was used, except that the poly(fluoroalkyl) sugar reagent 32 was substituted for Reagent 8. The amount of chymotrypsin immobilized was 8.6 mg per gram of particles, and the total activity was 1.0 IU per gram of particles. The retention of enzymatic activity after immobilization was 40% of the original activity.

EXAMPLE 4

Immobilization of Chymotrypsin Using 4'-(N-Oxysuccinimidylcarbonyl)Butyl 2,3,4,6-Tetra-O-(3-Perfluorooctyl)Propionyl-β-D-Glucopyranoside) and Neutral Fluorosurfactant Fluorocarbon particles (0.5 g) were activated with poly(fluoroalkyl) sugar reagent 8, as described in Example 1. To immobilize the enzyme, 5.0 mL of a 1 mg/mL chymotrypsin solution in pH 7.5 MOPS buffer, containing 0.05% Zonyl FSN, was added to the particles. Chymotrypsin activity was determined spectrophotometrically by measuring the increase in absorbance at 256 nm resulting from the hydrolysis of benzoyl-L-tyrosine-ethyl ester (BTEE). The assay mixture contained 1.5 mL of 0.08 Tris-HCl buffer, pH 7.8, with 0.1M calcium chloride, and 1.4 mL of 1.07 mM BTEE in 50% methanol.

The addition of the fluorosurfactant to the enzyme solution did not affect the amount of enzyme immobilized. However, the retention of activity increased to 50%.

EXAMPLE 5

Penicillin Amidase Immobilization Using 4'-(N-Oxysuccinimidylcarbonyl)Butyl 2,3,4,6-Tetra-O-(3-Perfluorooctyl)Propionyl-β-D-Glucopyranoside)

One gram of fluorocarbon particles was activated with poly(fluoroalkyl) sugar reagent 8 as described in Example 1.

For penicillin amidase immobilization, the stock enzyme solution (950 IU/mL, 81.5 mg protein/mL) was diluted ten-fold with 0.1 M, pH 7.5 MOPS buffer. Two milliliters of this enzyme solution was added to one gram of activated particles, and the suspension was stirred for 2 h at room temperature. The particles were washed three times using 0.02M, pH 8.0 phosphate buffer. The amount of protein immobilized was determined from the depletion of enzyme activity from the original enzyme solution and the activity present in the washes.

Penicillin amidase activity was determined using a method based on the transformation of penicillin G into 6-aminopenicillinate and phenylacetic acid, catalyzed by penicillin amidase. The rate of the reaction was determined using a pH Stat to measure the rate of consumption of sodium hydroxide. The substrate sodium penicillin G was dissolved in 0.02M, pH 8.0 phosphate buffer to give a 5% solution. Ten milliliters of the substrate solution was added to the reaction vessel of the pH Stat, and 50 uL of enzyme solution was added. The rate of addition of 0.1M sodium hydroxide solution, required to maintain a pH of 8.00, was recorded for 10 min. The specific activity of the enzyme was calculated from the measured reaction rate. The immobilized enzyme activity was determined in the same way as the soluble enzyme, using 100 uL of the settled particles in 10.0 mL of the substrate solution. The particles were collected, washed with water, and dried after completion of the assay.

The amount of penicillin amidase immobilized was 5.6 mg per gram of support, and the retention of activity was 51%. In control experiments in which the fluorocarbon particles were not treated with the sugar reagent, 8.6 mg of penicillin amidase was adsorbed onto the fluorocarbon particles, but no enzymatic activity was detectable.

EXAMPLE 6

Immobilization of Penicillin Amidase on Porous Silica Treated with Fluorosilanes

A. Preparation of Porous Silica Based Support

Fifty grams of silica gel (Zorbax TM PSM 300) coated with zirconium oxide by the procedure as described in Stout U.S. Pat. No. 4,600,646, incorporated herein by reference, were heated and stirred in a mixture of 350 mL of toluene and 40 mL of dimethylformamide (DMF) containing 57 g of imidazole under a Dean-Stark trap. A 50-mL fraction of the distillate was removed and the residual silica mixture was allowed to cool to approximately 50° C. To attach a fluorosilane interlayer onto the silica, the Dean-Stark trap was removed and 80 g of heptadecafluoro-1,1,2,2-tetrahydrodecyldichloromethyl silane (HDF-silane) was added to the silica mixture. The silica-HDF-silane mixture was refluxed for two hours, cooled and filtered. The HDF-silane-coated silica was then washed with 80% aqueous tetrahydrofuran (THF), resuspended in 350 mL of 80% aqueous THF and refluxed for 5 minutes. The HDF-silane-coated silica was cooled to 50° C., filtered and twice washed with 200 mL of THF per wash. The coated silica was resuspended in 350 mL of 80% aqueous THF, refluxed for 10 minutes, filtered, twice washed with 200 mL of THF per wash and twice washed with 200 mL of Freon ® TF per wash. The resulting coated silica was dried first in air and finally in a vacuum oven at 110° C.

B. Immobilization on Porous Silica

One gram of porous silica (Zorbax TM PSM300), treated with fluorosilane was activated with 100 mg of poly(fluoroalkyl) sugar reagent 8, as described in Example 1. The amount of protein immobilized, determined as described in Example 5, was 69 mg per gram of particles, and the retention of activity was 7%.

EXAMPLE 7

Immobilization of Protein A Using 4'(N-Oxysuccinimidylcarbonyl)Butyl 2,3,4,6-Tetra-O-(3-Perfluorooctyl)Propionyl-β-D-Glucopyranoside 8

One gram of fluorocarbon particles was washed twice with 10 mL portions of HPLC-grade acetone. The particles were then washed twice with 10 mL portions of acetone/water (1:1 v/v). After the washes, the solution above the settled particles was removed with a disposable pipet. Poly(fluoroalkyl) sugar reagent 8 (3 or 4 mg) was dissolved in acetone (2 mL), and water (2 mL) was slowly added to give an acetone/water (1:1 v/v) solution. At this point the solution may become slightly cloudy. The reagent mixture (4 mL) was added to 1 gram of the washed particles and the suspension was stirred for 30–60 minutes at room temperature to immobilize the reagent onto the particles. After this time, the particles were washed three times with 10 mL portions of acetone/water (1:1 v/v), followed by three washes with 10 mL portions of cold 0.1M sodium phosphate buffer, pH 8.5. During the buffer wash the particles were stirred gently to prevent the entrapment of air within the particles, which causes them to float.

Protein A was immobilized by adding 1.4 or 1.8 mL of a cold protein A solution (5 mg/mL) in 0.1M sodium phosphate buffer, pH 8.5, to the activated particles, and stirring the mixture overnight at 4° C. After immobilization, the particles were washed three times with 5 mL portions of 0.1M sodium phosphate buffer, pH 8.5, followed by washing five times with 5 mL portions of 0.2% Zonyl ® FSN fluorosurfactant in 0.1M sodium phosphate buffer, pH 8.5. Finally, the particles were washed three times with 5 mL portions of 0.1M sodium phosphate buffer, pH 8.5.

The amount of protein A immobilized onto the particles was determined by measuring the amount of protein remaining in the solution after immobilization and in the washes, using a colorimetric protein assay.

The activity of immobilized protein A was determined by measuring the binding of human immunoglobulin (hIgG) to protein A at pH 8.0, followed by release of the hIgG at pH 3.0. The particles with immobilized protein A were quantitatively packed into a small (1.25 mL) polypropylene chromatography column which was connected to a pump, set at a flow rate of 2.0 mL/min, and a UV detector, set at 280 nm, equipped with a recording integrator. The column was first equilibrated with 3 mL of 0.1M sodium phosphate buffer, pH 8.0, and a baseline was established for the integrator. Then 2.5 mL of a 10 mg/mL solution of hIgG in 0.1M sodium phosphate buffer, pH 8.0, was pumped onto the column followed by 5.5 mL of the buffer. Finally, 5 mL of 0.1M glycine-HCl buffer, pH 3.0, was pumped through the column to release the bound hIgG. The binding capacity of the immobilized protein A for hIgG was calculated by multiplying the amount of hIgG loaded onto the column (25 mg) with the area integrated for the released hIgG (as a fraction of the total integrated area). The volume of particles in the column was determined and the hIgG binding capacity recalculated as mg/mL.

| | Results: | | | |
|---|---|---|---|---|
| Experiment | Poly(fluoroalkyl) sugar reagent (mg) | Protein A (mg) | Immobilized protein A (mg) | Binding capacity for hIgG (mg/mL) |
| 1 | 3 | 7 | 3.0 | 9.0 |
| 2 | 3 | 9 | 3.5 | 12.0 |
| 3 | 4 | 7 | 5.5 | 9.2 |
| 4 | 4 | 9 | 6.9 | 11.3 |

EXAMPLE 8

Immobilization of Protein A Using N-3'-(N-Oxysuccinimidylcarbonyl)Propyl 2,3,4,5,6-Penta-O-(3-Perfluorooctyl)Propionyl Gluconamide 25

The procedure described in Example 7 was used, except that the poly(fluoroalkyl) sugar reagent 25 was substituted for reagent 8.

| | Results: | | | |
|---|---|---|---|---|
| Experiment | Poly(fluoroalkyl) sugar reagent (mg) | Protein A (mg) | Immobilized protein A (mg) | Binding capacity for hIgG (mg/mL) |
| 1 | 3 | 7 | 3.2 | 9.2 |
| 2 | 3 | 9 | 3.8 | 9.5 |
| 3 | 4 | 7 | 4.7 | 11.4 |
| 4 | 4 | 9 | 5.5 | 11.4 |

EXAMPLE 9

Immobilization of Protein A Using N-3'-(N-Oxysuccinimidylcarbonyl)Propyl 2,3,4,5,6,-Hexa-O-(3-Perfluorooctyl)Propionyl Glucoheptanamide 32

The procedure described in Example 7 was used, except that the poly(fluoroalkyl) sugar reagent 32 was substituted for reagent 8.

| | Results: | | | |
|---|---|---|---|---|
| Experiment | Poly(fluoroalkyl) sugar reagent (mg) | Protein A (mg) | Immobilized protein A (mg) | Binding capacity for hIgG (mg/mL) |
| 1 | 3 | 7 | 3.0 | 6.7 |
| 2 | 3 | 9 | 4.7 | 10.7 |
| 3 | 4 | 7 | 4.0 | 5.2 |
| 4 | 4 | 9 | 3.0 | 5.0 |

EXAMPLE 10

Immobilization of Protein G Using 4'(N-Oxysuccinimidylcarbonyl)Butyl 2,3,4,6-Tetra-O-(3-Perfluorooctyl)Propionyl-β-D-Glucopyranoside 8

The procedure described in Example 7 was used, except that protein G was substituted for protein A.

| | Results: | | | |
|---|---|---|---|---|
| Experiment | Poly(fluoroalkyl) sugar reagent (mg) | Protein G (mg) | Immobilized protein G (mg) | Binding capacity for hIgG (mg/mL) |
| 1 | 4 | 4 | 2.7 | 7.9 |
| 2 | 4 | 9.5 | 3.8 | 11.0 |

As many differing embodiments of this invention may be made without departing from the spirit and scope thereof, it is to be understood that this invention is not limited to the specific embodiments exemplified except as defined by the appended claims.

We claim:

1. A composition of the structure:

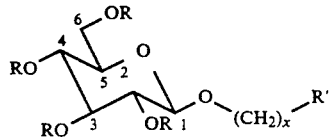

wherein

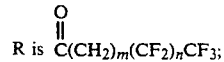

$m = 1-5$; $n = 3-20$;
$x = 1-10$; and
R' is selected from the following structures:

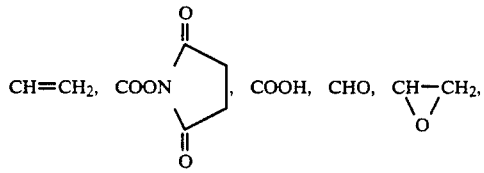

CONHNH$_2$, CH$_2$NH$_2$, and CH$_2$NHCOOCH$_2$Ph.

2. A composition of the structure:

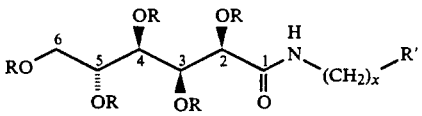

wherein
R is $CO(CH_2)_m(CF_2)_nCF_3$;
$x = 1-10$;
$m = 1-5$;
$n = 3-20$; and
R' is selected from

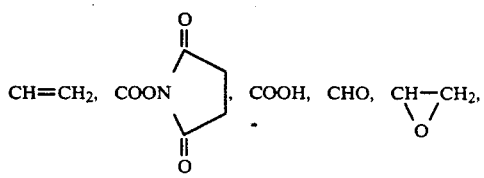

CONHNH$_2$, CH$_2$NH$_2$, and CH$_2$NHCOOCH$_2$Ph.

3. A composition of the structure:
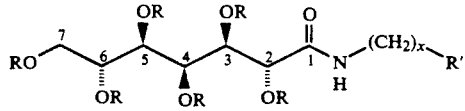
wherein
R is $CO(CH_2)_m(CF_2)_nCF_3$;
m is 1-5;
n is 3-20;
x = 2-10; and
R' is selected from
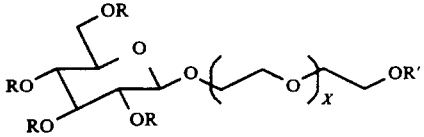
$CONHNH_2$, $CH_2NH_2$, and $CH_2NHCOOCH_2Ph$.
4. A composition of the structure:
wherein
R is $CO(CH_2)_m(CF_2)_nCF_3$;
m = 1-5;
n = 3-20.
R' is selected from $CH_2OCH_2Ph$, H, phenyl, $CH_3$ and $C_2H_5$;
x = 1-20.
* * * * *